(12) United States Patent
Nothacker et al.

(10) Patent No.: US 11,006,895 B2
(45) Date of Patent: May 18, 2021

(54) METHOD AND SYSTEM FOR TRANSDERMAL ALCOHOL MONITORING

(71) Applicant: KHN Solutions, Inc., San Francisco, CA (US)

(72) Inventors: Keith Harry Nothacker, San Francisco, CA (US); William Tammen, San Francsico, CA (US); Raymond Kampmeier, San Francisco, CA (US)

(73) Assignee: KHN Solutions, Inc., San Francisco, CA (US)

( * ) Notice: Subject to any disclaimer, the term of this patent is extended or adjusted under 35 U.S.C. 154(b) by 0 days.

(21) Appl. No.: 16/362,444

(22) Filed: Mar. 22, 2019

(65) Prior Publication Data
US 2019/0290197 A1 Sep. 26, 2019

Related U.S. Application Data

(60) Provisional application No. 62/646,706, filed on Mar. 22, 2018.

(51) Int. Cl.
*A61B 5/00* (2006.01)
*A61B 5/145* (2006.01)
(Continued)

(52) U.S. Cl.
CPC ........ *A61B 5/4845* (2013.01); *A61B 5/14546* (2013.01); *A61B 5/681* (2013.01);
(Continued)

(58) Field of Classification Search
CPC ... A61B 5/4845; A61B 5/14546; A61B 5/681; A61B 5/6833; A61B 5/0002; A61B 5/097; A61B 5/6824
See application file for complete search history.

(56) References Cited

U.S. PATENT DOCUMENTS 5,220,919 A 6/1993 Phillips et al.
5,426,415 A 6/1995 Prachar et al.
(Continued)

OTHER PUBLICATIONS

Kim, J et al. Noninvasive alcohol monitoring using a wearable tattoo-based ontophoretic-biosensing system. ACS Sensors. Jul. 12, 2016. vol. 1. No. 8; abstract.
(Continued)

*Primary Examiner* — Mohamed Barakat
(74) *Attorney, Agent, or Firm* — Jeffrey Schox; Caitlin Ploch

(57) ABSTRACT

A method for monitoring intoxication of a user, the method including: receiving a set of samples from a body region of a user; generating an intoxication metric based on the set of samples; and providing a notification to the user based on the intoxication metric. The method can additionally or alternatively include: modifying operation of the transdermal alcohol sensing device based on the intoxication metric; determining contextual data; maintaining a hydration level of the transdermal alcohol sensing device; and any other suitable processes. A system for monitoring intoxication of a user including a sensor and a housing. The system can additionally or alternatively include any or all of: an inlet, a fastener, an electronics subsystem, a user device, and/or any other suitable component.

18 Claims, 13 Drawing Sheets

(51) Int. Cl.
*A61B 10/00* (2006.01)
*A61B 5/097* (2006.01)

(52) U.S. Cl.
CPC ........ *A61B 5/6833* (2013.01); *A61B 10/0064* (2013.01); *A61B 5/0002* (2013.01); *A61B 5/097* (2013.01); *A61B 5/6824* (2013.01); *A61B 2010/0009* (2013.01); *A61B 2010/0087* (2013.01)

(56) References Cited

U.S. PATENT DOCUMENTS

| | | |
|---|---|---|
| 5,944,661 A | 8/1999 | Swette et al. |
| 6,026,674 A | 2/2000 | Gammenthaler |
| 6,075,444 A | 6/2000 | Sohege et al. |
| 6,853,956 B2 | 2/2005 | Ballard et al. |
| 6,956,484 B2 | 10/2005 | Crespo |
| 7,256,700 B1 | 8/2007 | Ruocco et al. |
| 7,311,665 B2 | 12/2007 | Hawthorne et al. |
| 7,462,149 B2 | 12/2008 | Hawthorne et al. |
| 7,611,461 B2 | 11/2009 | Hawthorne et al. |
| 7,641,611 B2 | 1/2010 | Hawthorne et al. |
| 7,930,927 B2 | 4/2011 | Cooper et al. |
| 7,934,577 B2 | 5/2011 | Walter et al. |
| 8,078,334 B2 | 12/2011 | Goodrich |
| 8,165,824 B2 | 4/2012 | Iiams et al. |
| 8,240,419 B2 | 8/2012 | Zimmermann et al. |
| 8,317,697 B2 | 11/2012 | Hawthorne et al. |
| 8,381,573 B2 | 2/2013 | Keays |
| 8,505,360 B2 | 8/2013 | Ruocco et al. |
| 8,657,744 B2 | 2/2014 | Rompa et al. |
| 8,707,758 B2 | 4/2014 | Keays |
| 8,862,152 B1 | 10/2014 | Buchholz et al. |
| 8,957,771 B2 | 2/2015 | Arringdale et al. |
| 9,228,997 B2 | 1/2016 | Keays |
| 9,239,323 B2 | 1/2016 | Keays |
| 9,241,659 B2 | 1/2016 | Rompa et al. |
| 9,417,232 B2 | 8/2016 | Keays et al. |
| 9,442,103 B1 | 9/2016 | Goad |
| 9,481,245 B2 | 11/2016 | Nelson |
| 9,489,487 B2 | 11/2016 | Hawthorne et al. |
| 9,746,456 B2 | 8/2017 | Keays |
| 9,829,480 B2 | 11/2017 | Wojcik et al. |
| 9,855,000 B2 | 1/2018 | Lansdorp et al. |
| 9,881,997 B2 | 1/2018 | Sakata et al. |
| 9,922,508 B2 | 3/2018 | Keays et al. |
| 10,040,349 B2 | 8/2018 | Devries et al. |
| 2003/0177119 A1* | 9/2003 | Cole ............ G06F 16/273 |
| 2006/0237252 A1* | 10/2006 | Mobley ........... B60K 28/063 |
| | | 180/272 |
| 2013/0218039 A1* | 8/2013 | Sotos ............. A61B 7/003 |
| | | 600/529 |
| 2014/0365142 A1* | 12/2014 | Baldwin ........... A61B 5/683 |
| | | 702/24 |
| 2016/0338627 A1 | 11/2016 | Lansdorp et al. |
| 2017/0086714 A1* | 3/2017 | Nothacker ........ G06F 19/00 |
| 2017/0231571 A1* | 8/2017 | Rogers ........... A61B 5/6833 |
| | | 600/301 |
| 2017/0354354 A1 | 12/2017 | Nothacker et al. |
| 2018/0209955 A1* | 7/2018 | Moeller .......... A61B 5/4845 |
| 2018/0263538 A1* | 9/2018 | Heikenfeld ...... A61B 5/14521 |
| 2019/0246958 A1 | 8/2019 | Moeller et al. |

OTHER PUBLICATIONS

Kuswandi, B et al. A simple visual ethanol biosensor based on alcohol oxidase immobilized onto polyaniline film for halal verification of fermented beverage samples. Sensors. 2014. vol. 14. No. 2; p. 2144, figure 6.

Zettl, Robert J., "The Determination of Blood Alcohol Concentration by Transdermal Measurement", Commissioned by Alcohol Monitoring Systems, Inc., Highlands Ranch, Colorado, Jul. 2002, 13 pages.

* cited by examiner

METHOD AND SYSTEM FOR TRANSDERMAL ALCOHOL MONITORING

CROSS-REFERENCE TO RELATED APPLICATIONS

This application claims the benefit of U.S. Provisional Application Ser. No. 62/646,706, filed 22 Mar. 2018, which is incorporated in its entirety by this reference.

This application is related to U.S. application Ser. No. 16/218,357, filed 12 Dec. 2018, which is continuation of U.S. application Ser. No. 15/666,062, filed 1 Aug. 2017, which is a continuation of U.S. application Ser. No. 15/375,801, filed 12 Dec. 2016, each of which is incorporated herein in its entirety by this reference.

TECHNICAL FIELD

This invention relates generally to the intoxication monitoring device field, and more specifically to a new and useful method and system for transdermal alcohol monitoring.

BACKGROUND

Alcohol use remains the third leading cause of death both in the USA (85,000 deaths annually) and worldwide (up to 2.5 million deaths annually). The economic costs associated with excessive drinking exceed $223 billion annually in the USA alone. Some of the objective methods for measuring alcohol, such as breathalyzers and biological assays, can have significant drawbacks, such as invasiveness, constant user interaction, and/or the inability to provide real-time (or near real-time) quantitative measurements of alcohol usage (e.g., as opposed to metabolites). Transdermal alcohol detection, which measures alcohol permeating through the skin and correlates that measurement to the blood alcohol concentration, can offer the capacity to provide a noninvasive, continuous, and quantitative measurement of bodily alcohol. Thus, there is a need in the intoxication monitoring field to create an improved transdermal alcohol monitoring system and method.

This invention creates such a new and useful transdermal alcohol monitoring system and method.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview

Figure 2:
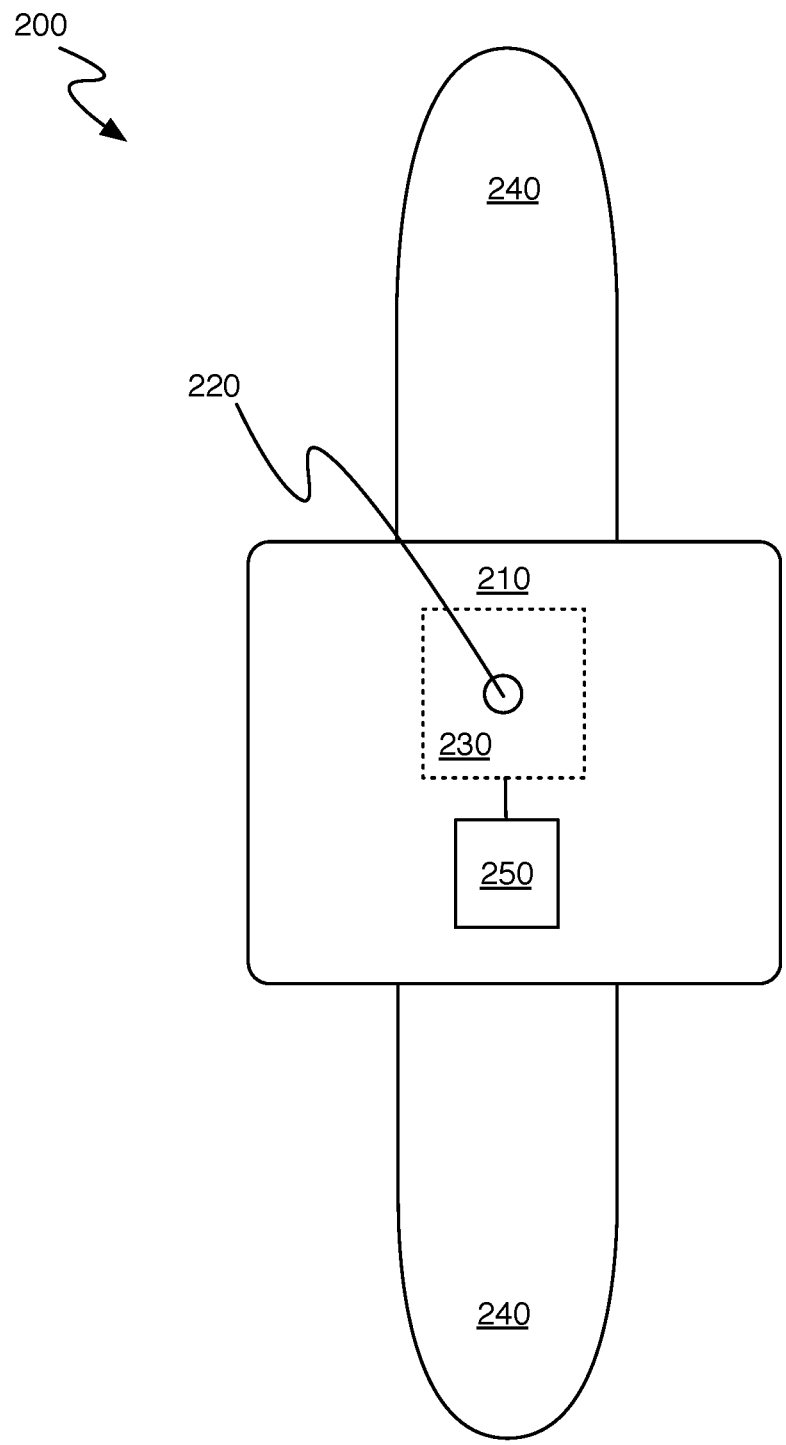
FIG. 2 depicts an example embodiment of a system for transdermal alcohol monitoring.

As shown in FIG. 2, an embodiment of a system 200 for monitoring intoxication of a user preferably includes: a housing 210, an inlet 220, a sensor 230, a fastener 240, and an electronics subsystem 250. Additionally or alternatively, the system can include or be configured to interact with a user device, or any other suitable component. The system 200 functions to enable transdermal measurements of the user's blood alcohol content by sensing alcohol (e.g., ethanol) near a user's skin, preferably continuously and in near real time.

The system 200 functions to enable continuous or near-continuous monitoring of a user's intoxication level, which can in turn function to provide any number of suitable triggers, notifications, or other actions based on the intoxication level. For a high-risk user (e.g., user on probation, user with a history of a DUI, user deemed to be at risk to himself or other, user diagnosed as an alcoholic, etc.) this can enable the user to live outside of a facility (e.g., correctional facility, rehabilitation facility, etc.) while still being closely monitored, determine at an early time point when the user may be in danger or in violation of a sobriety plan, or otherwise intoxicated. For moderate or low-risk users (e.g., conscientious users, etc.), the system can function to optimize a night out (e.g., plan a timing of drinking events) for a user, present a user with easy-to-interpret intoxication assessments (e.g., graphical displays or other visual indicators), or provide any other output.

Figure 1:
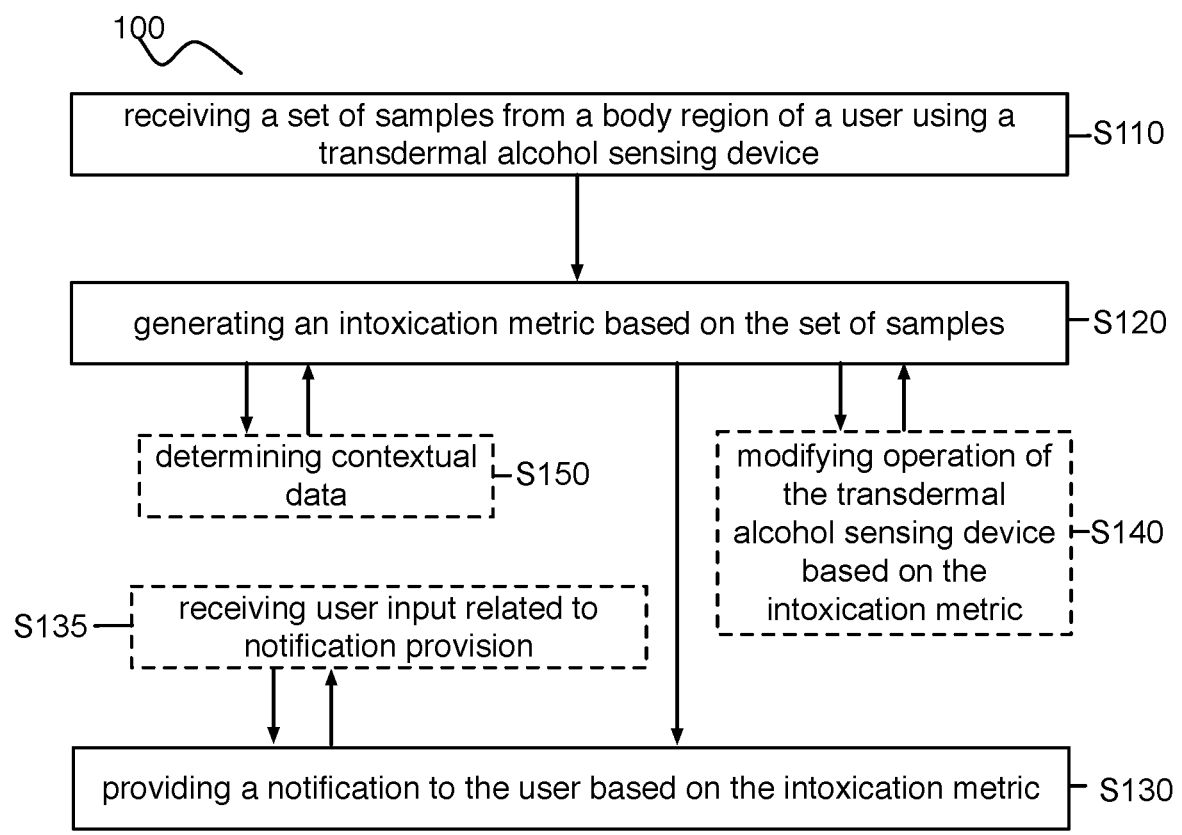
FIG. 1 depicts a flow chart of an embodiment of a method for transdermal alcohol monitoring.

As shown in FIG. 1, an embodiment of a method 100 for intoxication monitoring includes: receiving a set of samples from a body region of a user using a transdermal alcohol sensing device S110; generating an intoxication metric based on the set of samples S120; and providing a notification to the user based on the intoxication metric S130. The method 100 can additionally or alternatively include: modifying operation of the transdermal alcohol sensing device based on the intoxication metric S140; and determining contextual data S150.

The method 100 functions to provide intoxication monitoring to a user in substantially real time during a drinking session. A drinking session is preferably a period of time (e.g., a time window) during which a user is consuming alcoholic beverages and/or blood alcohol levels continue to be elevated (e.g., at a level above 0.00 BAC after consuming one or more alcoholic beverages, at a level above a threshold level such as 0.01, 0.02, 0.08, etc.), but can additionally or alternatively include any other suitable period of time. The method 100 can also function to provide alcohol monitoring capability to a remote entity associated with the user (e.g., a parole officer, a parent, a friend, an accountability acquaintance, etc.).

The method can include aggregating data (e.g., intoxication metric time series) at a database. Aggregated data can be used as a training dataset for building models of user intoxication state and/or related parameters in relation to a wide range of factors. Building models of breathalyzer sensor state based on training data can be performed using any suitable machine learning algorithm(s). In variations, the machine learning algorithm(s) can be characterized by a learning style including any one or more of: supervised learning (e.g., using logistic regression, using back propagation neural networks), unsupervised learning (e.g., using an Apriori algorithm, using K-means clustering), semi-supervised learning, reinforcement learning (e.g., using a Q-learning algorithm, using temporal difference learning), and any other suitable learning style. Furthermore, the machine learning algorithm can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial lest squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), and any suitable form of machine learning algorithm. As such, models of user intoxication state can be used to inform analyses associated with subsequent sensor readings.

Figure 4:
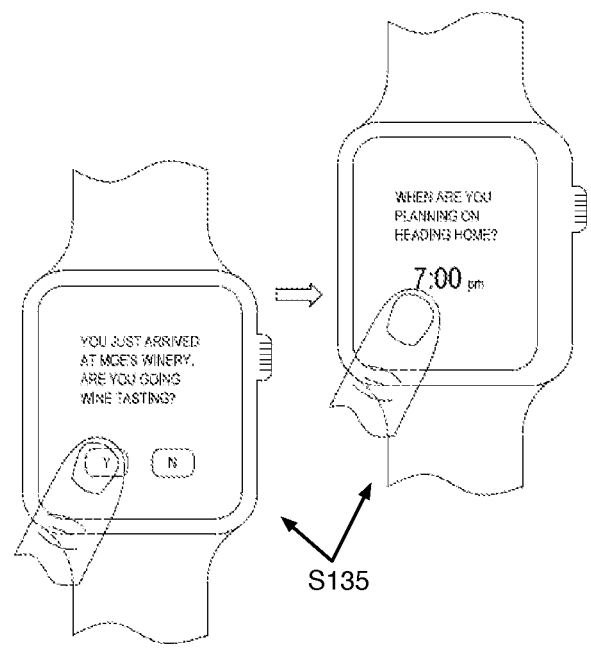
FIG. 4 depicts a schematic illustration of an example of a portion of a method for transdermal alcohol monitoring.

In a first example, as shown in FIG. 4, the method 100 can include determining that a user may consume more alcohol than safe or desired (e.g., at a winery tasting room, at a college party, etc.) and presenting recommendations to the user (e.g., stop drinking at a time that will allow the user to become sober before needing to drive, reduce the rate of drinking to avoid health risks, etc.).

In a second example, the method 100 can include determining correlations between drinking events (e.g., sipping detected based on accelerometer data) and blood alcohol content and/or user performance on intoxication tests (e.g., puzzles, speech clarity, pupil dilation), presenting the correlations to the user, and/or preventing user actions (e.g., placing phone calls or sending text messages to predetermined contacts).

In a third example, the method 100 can include detecting user intoxication (e.g., through a worn alcohol sensor and/or an alcohol sensor integrated into a piece of equipment, such as a steering wheel of a vehicle or a sensor associated with an employee time logging system) and, in response to detecting intoxication, providing a warning (e.g., to the user, to a supervisor of the user, etc.) and/or preventing use of the equipment.

In a fourth example, the method 100 can include presenting a visual indication of a user's ongoing sobriety (e.g., units of time such as days, weeks, or years since the user's last drinking event; awards associated with sobriety; etc.).

In a fifth example, the method 100 can include presenting a visual indication of a user's current intoxication to another person (e.g., bartender) and/or preventing alcohol purchases by intoxicated users.

In a sixth example, the method 100 can include determining a user's current, past, and/or projected intoxication and/or presenting an indication (e.g., visual indication, such as a numerical value, directed arrow, trendline, etc.) of the intoxication (e.g., to the user, at a wearable electronic device, etc.).

The method 100 can be implemented, at least in part, using embodiments, variations, and/or examples of the system 200 described below, wherein the system is configured to be used outside of a "law enforcement setting", and instead, used by users in their normal daily lives.

In variations, the system 200 can be configured to perform at least a portion of the method 100 described below, and can additionally or alternatively be configured to perform any suitable method for collecting and/or analyzing biological samples indicative of blood alcohol content.

The system 200 can additionally or alternatively include one or more embodiments, variations, and examples of system elements (e.g., transdermal alcohol sensing device components, mobile computing device components, computing system components, etc.) described in U.S. application Ser. No. 14/169,029 entitled "Method and System for Monitoring Intoxication" and filed on 30 Jan. 2014, U.S. application Ser. No. 14/602,909 entitled "Method and System for Remotely Monitoring Intoxication" and filed on 22 Jan. 2015, U.S. application Ser. No. 14/631,125 entitled "Method and System for Monitoring Intoxication" and filed on 25 Feb. 2015, and U.S. application Ser. No. 15/375,801 entitled "Wearable System and Method for Monitoring Intoxication" and filed on 12 Dec. 2016, each of which is incorporated herein in its entirety by this reference. Variations of the system 100 can, however, be implemented at least in part using any other suitable system elements.

Additionally or alternatively, variations of the system 200 can be configured such that the user can select between information that is optimized for speed and information that is optimized for accuracy. For instance, information optimized for speed can be cause upon analyses of a peak of a breath sample signal, while information that is optimized for accuracy can be based upon analysis of the integrated area of a breath sample signal. Alternatively, the system 200 can be configured to automatically switch between different modes (e.g., speed mode, accuracy mode) based upon detected environmental conditions and/or any other suitable factors.

Additionally or alternatively, variations of the system 200 can interact with beacon systems (e.g., iBeacon, Estimote systems, etc.) in order to perform background functions, even when mobile applications associated with the system 100 are in an inactive state. In one example, the system 100 can be configured to enable background operations of the system 100 in line with the method 100 described above, whenever the system 100 interacts with a beacon system (e.g., if an iOS of an Apple device detects an iBeacon system). In an example operation of such a system 200, upon detection of a beacon system (e.g., using a BlueTooth LE advertising packet that facilitates invoking of devices when specific beacon types are detected), an individual can be prompted to turn on the breathalyzer device and/or select a notification on a mobile application associated with the breathalyzer device. Then, the breath sample provision process could be initiated within the application in a streamlined process. The beacon system can be associated with a specific environment.

Furthermore, variations of the method 100 can be implemented at least in part by one or more embodiments, variations, and examples of system elements described in U.S. application Ser. No. 14/169,029 entitled "Method and System for Monitoring Intoxication" and filed on 30 Jan. 2014, U.S. application Ser. No. 14/602,909 entitled "Method and System for Remotely Monitoring Intoxication" and filed on 22 Jan. 2015, and U.S. application Ser. No. 14/631,125 entitled "Method and System for Monitoring Intoxication" and filed on 25 Feb. 2015, each of which is incorporated herein in its entirety by this reference. However, the method 100 can additionally or alternatively be implemented using any other suitable system. Furthermore, the method 100 is preferably configured for processing of data associated with fuel cell sensors; however, the method 100 can additionally or alternatively be adapted for processing of data associated with semiconductor sensors and/or any other suitable sensors for processing samples associated with intoxication or substance use.

2. Benefits

Variations of the method and/or system can confer several benefits and/or advantages.

First, variants of the method and/or system can enable a user to know the amount of alcohol they have consumed during a drinking session, and can include notifying the user of the amount of alcohol consumed. For example, the method can include computing a number of standard alcoholic beverages (e.g., drinks) consumed based on a time-series of transdermal alcohol content (TAC) values, and displaying the number at a display of a mobile device associated with the user. In the same or a different example, the method can include determining a type of alcoholic beverage consumed by the user (e.g., beer vs. wine vs. cocktail vs. shot), which can function, for instance, to improve an accuracy of an estimated time point (e.g., time until sober, time until peak intoxication), or any other suitable parameter (e.g., blood alcohol content level at peak intoxication). In yet another example, the method can include computing a blood alcohol content (BAC) value associated with a user.

Second, variants of the method and/or system can enable determination of a peak intoxication metric value (e.g., BAC value) reached during a time window (e.g., time period). The time window can be a current time window associated with an ongoing drinking session, a past time window associated with a historical drinking session, and/or a time window associated with a future time period (e.g., a future drinking session, a non-drinking session, etc.).

Third, variants of the method and/or system can enable continuous determination (e.g., tracking, monitoring) of an intoxication metric value (e.g., BAC value, TAC value) of a user, in order to generate a curve of intoxication metric value versus time associated with a user (e.g., during a drinking session). Alternatively or additionally, variants of the system and/or method can extrapolate the intoxication metric between data collection timestamps (e.g., between two known intoxication metric values; extrapolate a predicted intoxication metric value; etc.). This can function, for instance, to better understand complex and/or persisted impacts of alcohol on health (e.g., caloric intake, recovery time after a night of drinking, sleep, etc.), as intoxication and its associated parameters (e.g., duration, timing, amount of alcohol, speed of consumption, etc.) can affect any or all of: blood pressure, arrhythmia, resting heart rate, mobilization of fat and/or nutrients absorbed, dehydration, physical fitness parameters (e.g., lactic acid buildup, exercise intensity, maximum heart rate, etc.), or any number of other parameters. By better understanding these effects for a single user and/or an aggregated set of users, more accurate intoxication guidelines, warnings, and predictions of potential threats to intoxicated individuals can be determined.

In one set of examples, for instance, continuous or near-continuous monitoring is enabled by a system in the form of a wearable wristband configured to receive transdermal samples (e.g., vapor, ethanol vapor, sweat, insensible perspiration, sensible perspiration, etc.) from a skin surface user and determine TAC values based on the transdermal samples. The TAC values can then optionally be used to determine any or all of: BAC values, a number of drinks a user has consumed (e.g., for a drinking session, over a predetermined time window, etc.), a type of drink the user has consumed, an actual or predicted time point (e.g., time at which user began drinking, time at which user consumed a drink, predicted time at which user will reach peak intoxication, predicted time at which user will reach sobriety, etc.), or any other suitable parameter.

In a specific example, the system and/or method can predict when the BAC will fall below a predetermined value (e.g., 0.08%, the legal limit, a manually-set value, 0.00%, a value associated with sobriety, etc.). In specific examples, the TAC curve (or value) can be used to determine a BAC curve (or value), wherein the estimated time at which the BAC value falls below the predetermined value can be estimated from the BAC or TAC curve (or value) using the method disclosed in U.S. application Ser. No. 15/979,220 filed 14 May 2018 (incorporated herein in its entirety by this reference), or using any other suitable method.

In another set of examples, continuous remote monitoring can be especially beneficial in the case of high risk individuals, enabling faster response times in the event that a user exceeds a threshold intoxication level and preventing potential harm to the user or others (e.g., by notifying a monitoring agency, providing instructions to the user, disabling a user's access to a vehicle, etc.).

In yet another set of examples, the system and/or method can enable the prediction of a peak intoxication state (e.g., peak TAC value and associated time peak is reached, peak BAC value and associated time peak is reached, etc.) or any other suitable predetermined intoxication state (e.g., a predetermined TAC or BAC value, etc.), which can function, for instance, to assist a user in planning his or her evening. The peak can be determined based on any or all of: a current intoxication level, a drinking plan, a sample parameter (e.g., volume of sweat), or any other suitable parameter. The peak is preferably dynamically updated (e.g., based on a current intoxication value, based on a user input for planned drink consumption, based on a user input classifying a drink just consumed, etc.), but can alternatively be static, updated at a predetermined interval (e.g., every hour), updated continuously, or otherwise determined. In a specific example, a user can use a predicted peak to determine whether or not to consume another drink.

Fourth, variants of the method and/or system can enable real-time notification of a user's intoxication level, thereby improving users' ability to moderate their alcohol consumption. For example, the method can include determining that a user has consumed a number of drinks exceeding a threshold number (e.g., set by the user as a preference) and notifying a user in response to determining that the threshold number has been exceeded. In another example, the method can include determining that a rate of alcohol consumption has exceeded a threshold rate (e.g., based on demographics of the user) and transmitting a notification to an entity (e.g., the user, a monitoring agent) in response to the rate of alcohol consumption exceeding the threshold rate.

Fifth, variants of the method and/or system can enable an accurate and/or precise determination of a BAC value from a TAC value as measured from a skin surface (e.g., wrist region, arm region, shoulder region, etc.) of a user. In an example, for instance, a TAC value can be used to determine a BAC value with greater than 80% confidence (e.g., greater than 90% confidence, 95% confidence, etc.). The method and/or system can additionally or alternatively confer the benefit of determining a BAC value from a TAC value with minimal lag from the first time point of alcohol consumption until a first reading indicating an intoxication metric (e.g., actual intoxication, predicted intoxication, etc.) above baseline is determined and/or provided to the user (e.g., less than 20 minutes, less than 30 minutes, between 2 minutes and 1 hour, greater than 10 minutes, etc.).

Sixth, variants of the method can enable an improved (e.g., faster, more accurate, higher confidence, etc.) prediction and/or determination of alcoholism of a user. In some examples, for instance, continuous monitoring of a user's intoxication with the system and/or method can determine an intoxication parameter used to assess whether or not the user is an alcoholic. In a specific example, for instance, a rate of alcohol processing is determined and compared with a predetermined threshold (e.g., 0.015 grams per 100 milliliters per hour [g/100 mL/hr]), and if the determined rate is greater than the threshold, an assessment of alcoholism is attributed to the user. This can then serve, for instance, as a suitable trigger for any number of outcomes (e.g., call to a monitoring agency, notification to a user, recommendation to the user, etc.).

Seventh, variants of the method and/or system can enable the scheduling of a night out for a user or set of users, which can be optimized for any or all of: safety, convenience, cost (e.g., ensuring that a user can legally drive himself the entire night), timing (e.g., planned last drink time to ensure user reaches a legal level before bar closes), enjoyment (e.g., reaching and sustaining a baseline intoxication level, preventing a hangover, etc.), or any other suitable factor.

Eighth, variants of the method and/or system can enable an accurate reading and assessment of the effects of alcohol on a second factor, such as effects of alcohol use on the effectiveness of a drug being tested by a pharmaceutical company. In an example, for instance, the system and/or method can be used to determine how alcohol affects the effectiveness of a drug, which can provide more accurate data and robust analyses than current data (e.g., user self-reporting, infrequent urine tests, etc.).

Ninth, variants of the method and/or system can enable an integrated approach to intoxication analysis, utilizing information (e.g., user location information, user calendar, user history, user preferences, etc.) from additional information sources (e.g., client applications executing on a user device, web pages, etc.), which can function to provide instructions, notifications, and triggers of maximum usefulness to each user. In some examples of this variant, the integrated approach is enabled through a client application executing on a user device having access to other client applications executing on the user device. In one example, detecting that a user is located in a bar (e.g., based on GPS data of mobile phone) and that the user did not utilize a ride share service (e.g., by checking history of ride share application) to get to the bar, a notification can be provided to a user a set time before the bar closes to encourage the user to stop drinking so that he or she can legally drive home once the bar closes.

Tenth, variants of the method and/or system can enable a user to achieve and/or maintain a desired intoxication "sweet spot," such as any or all of: an ideal level of buzz for an extended period of time, a mitigation of hangovers, and a mitigation of the impact of drinking on user health (e.g., sleep, weight, fitness, wellness, etc.). In some examples, for instance, a continuously updated intoxication curve can be provided to a user to determine when and how often the user should drink to achieve a desired effect.

Eleventh, variants of the method and/or system can enable a consumer to track alcohol use for fun and out of curiosity. In some examples, for instance, the system and/or method can function to provide easy-to-interpret data (e.g., in the form of one or more graphical displays or other visual identifiers), which can then be shared with others (e.g., texted), uploaded to social media, used to plan a social event (e.g., meet-up at current bar where user is located), or otherwise used.

However, variants of the method and/or system can confer any other suitable benefits and/or advantages.

3. System

As shown in FIG. 2, an embodiment of a system 200 for monitoring intoxication of a user includes a sensor 230 and a housing 210. Additionally or alternatively, the system 200 can include any or all of: an inlet 220, a fastener 240, an electronics subsystem 250, a user device 260, and/or any other suitable component.

The system 200 preferably receives one or more inputs in the form of a biological sample (e.g., vapor from skin surface, ethanol vapor, sweat, breath, urine, saliva, blood, etc.) from a user. Biological samples are preferably received at a housing 210 of the system 200 but can additionally or alternatively be received at a secondary device (e.g., a breathalyzer), a user device, a remote server or database, or any other suitable location. The system 200 can additionally or alternatively receive other suitable inputs (e.g., settings, triggers between operation modes, user preferences, etc.), such as through one or more input elements (e.g., buttons, sliders, touch-sensitive surfaces, knobs, dials, etc.) of the system 200.

The system 200 preferably provides a set of one or more outputs to a user, which function to indicate an intoxication level of the user. In some variations, the outputs are provided at a housing 210 of the system (e.g., through a light emitter, vibration motor, speaker, etc.). Additionally or alternatively, outputs can be provided at a user device 260 or any other suitable component or system.

In variations of the system 200 including and/or configured to interact with (e.g., communicatively couple, wirelessly connect, etc.) a user device 260, any or all of the inputs and outputs can be received or provided, respectively, at the user device. In an example, for instance, an input in the form a biological sample is received at an inlet 220 of the system, an input in the form of a user schedule is received at a client application executing on a user device 260 wirelessly connected to the system, an output in the form of a blinking light is provided at a light emitter of the housing 210 (e.g., wherein a color, blinking frequency, and/or brightness indicates an intoxication level of the user), and an output in the form of a graphic display depicting an intoxication curve is provided at a display of a user device 260.

The sensor 230 functions to determine a signal (e.g., electrical signal) based on a set of one or more samples (e.g., biological samples) received from the user. The sensor 230 preferably includes a fuel cell sensor, but can additionally or alternatively include an enzymatic sensor, or any other suitable sensor. The sensor preferably receives one or more samples from a user, further preferably one or more biological samples. Additionally or alternatively, the sensor 230 can receive user information, environmental information, contextual information, or any other suitable information. The sensor can be removable from the system 200, or be permanently coupled to the system 200.

The system 200 can optionally include any number of supplementary sensors, which can function to receive environmental and/or contextual information. The supplementary sensors can include any or all of: a skin conductance sensor, temperature sensor, microphone (e.g., to determine an environment of a user, to recognize a noisy bar setting, to recognize the sound of a vehicle being operated, etc.), camera (e.g., to image surroundings of a user), other ambient environment sensors (e.g., humidity sensor, ambient light sensor, etc.), accelerometer or other kinematic sensor (e.g., to determine if a user is exercising to induce sweating), a biomonitoring sensor (e.g., heart rate monitor, electroencephalography sensor, etc.), or any other suitable sensor.

In one variation, the system 200 includes an accelerometer (e.g., in a transdermal alcohol sensing device, in a user device, in a breathalyzer device, etc.), which functions to measure a user's personal gait pattern and use the personal gait pattern as a unique identifier (e.g., in a two-factor authentication process). The gait pattern can then, for instance, be associated with an alcohol signal received at the device (e.g., contemporaneously with the gait pattern) having the accelerometer. A second verification signal (e.g., video of user displaying gait pattern and user's face for identification) can be taken as well to associate the user's identity with the gait pattern (e.g., determined through image analysis of video of the user walking). In a specific example, for instance, a sample received at a transdermal alcohol sensing device (e.g., wristband device) can be recorded contemporaneously (e.g., during an overlapping time period, with a delay of less than 1 minute, etc.) with a gait pattern received at an accelerometer in the transdermal alcohol sensing device. A second verification signal which associates the user's identity with the gait pattern can be recorded at a camera (e.g., of a user device). Based on these two authentication processes, it can be confirmed that the alcohol signal is associated with the appropriate user.

The housing 210 functions to support one or more components of the system 200, and to receive one or more samples (e.g., biological samples) from the user. Additionally or alternatively, the housing 210 can function to prevent ingress of matter from the environment (which could affect analysis of a biological sample, for instance), retain the system 200 against the user, or perform any other suitable function.

Figure 10A:
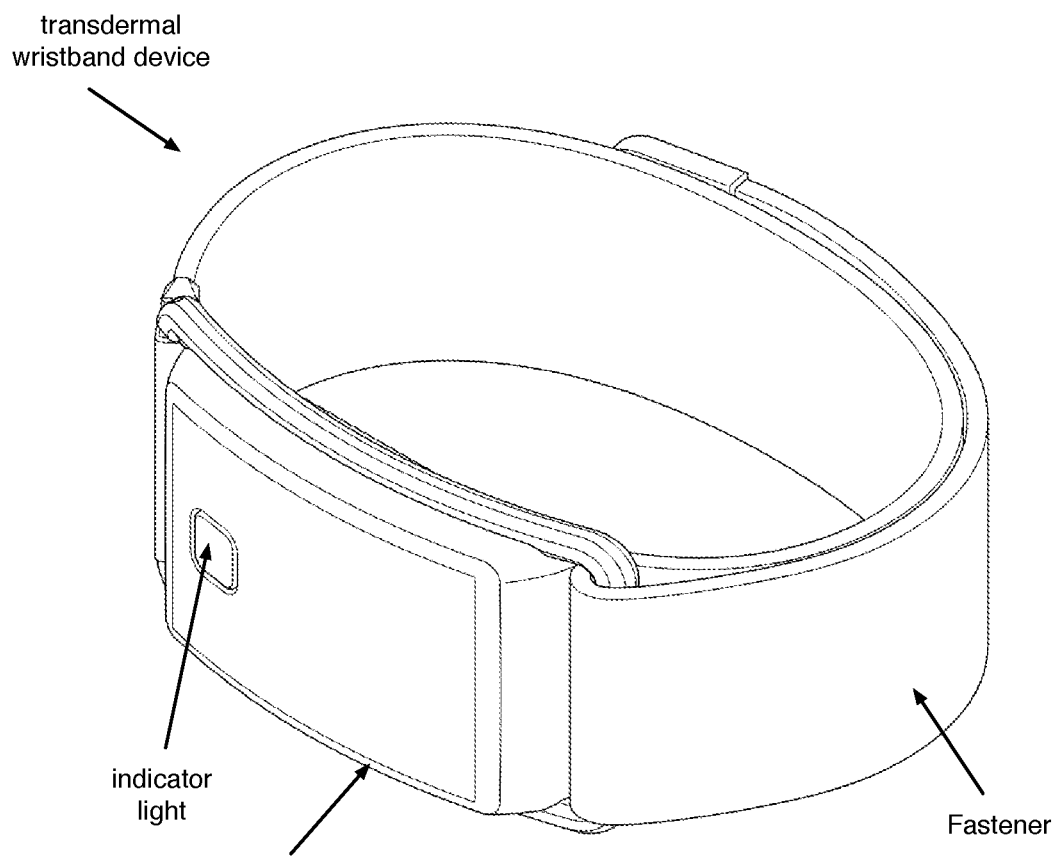
FIGS. 10A-10B depict an embodiment of the system.
Figure 10B:
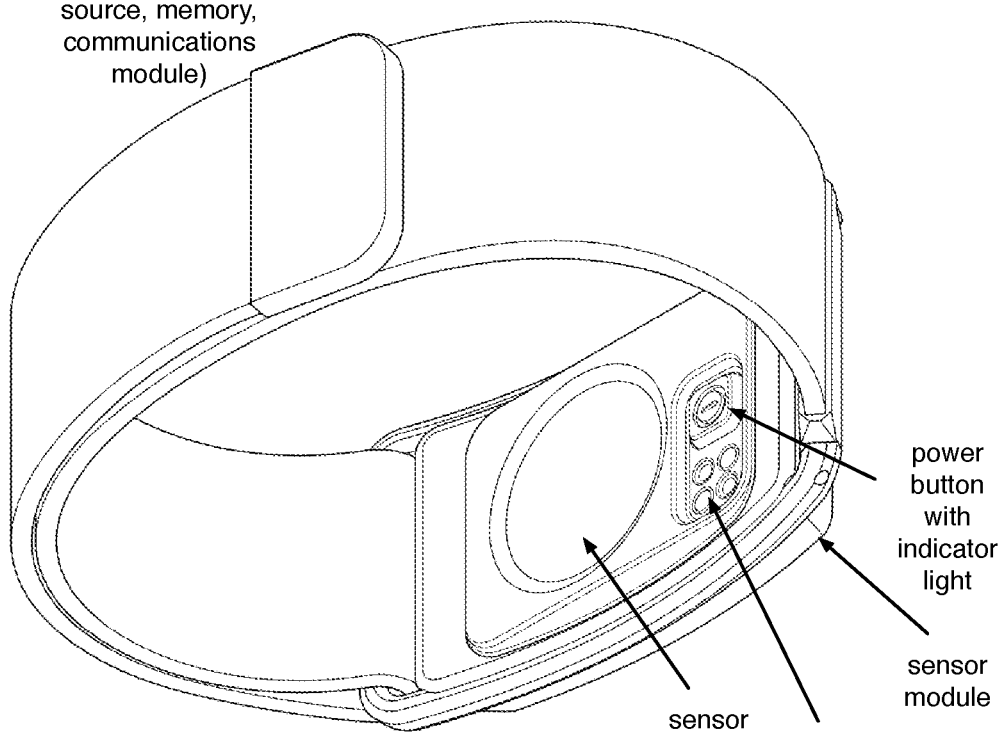

The system 200 can additionally include any or all of: a power source (e.g., rechargeable battery), memory, a processing system (e.g., processor, microprocessor, CPU, etc.), control module, a fastener (e.g., band, wristband, clip, etc.), a sealing mechanism (e.g., gasket) configured to create a gaseous seal between the sensor and the environment (e.g., to prevent particulate matter from being introduced to a transdermal sensor), or any other suitable component, In one variation of the system 200 (e.g., as shown in FIGS. 10A-10B, the system 200 includes a low energy (e.g., Bluetooth) wristband device configured to receive a transdermal sample from the skin surface of a wrist region of the user. A sensor 230 arranged in a housing of the wristband device receives an electrical signal corresponding to the transdermal sample, which is then used to determine a value of an intoxication parameter (e.g., TAC value, BAC value, etc.) at a processing system associated with any or all of: the wristband device, a user device in communication with the wristband device, a remote server, or any other suitable component or location.

Figure 12:
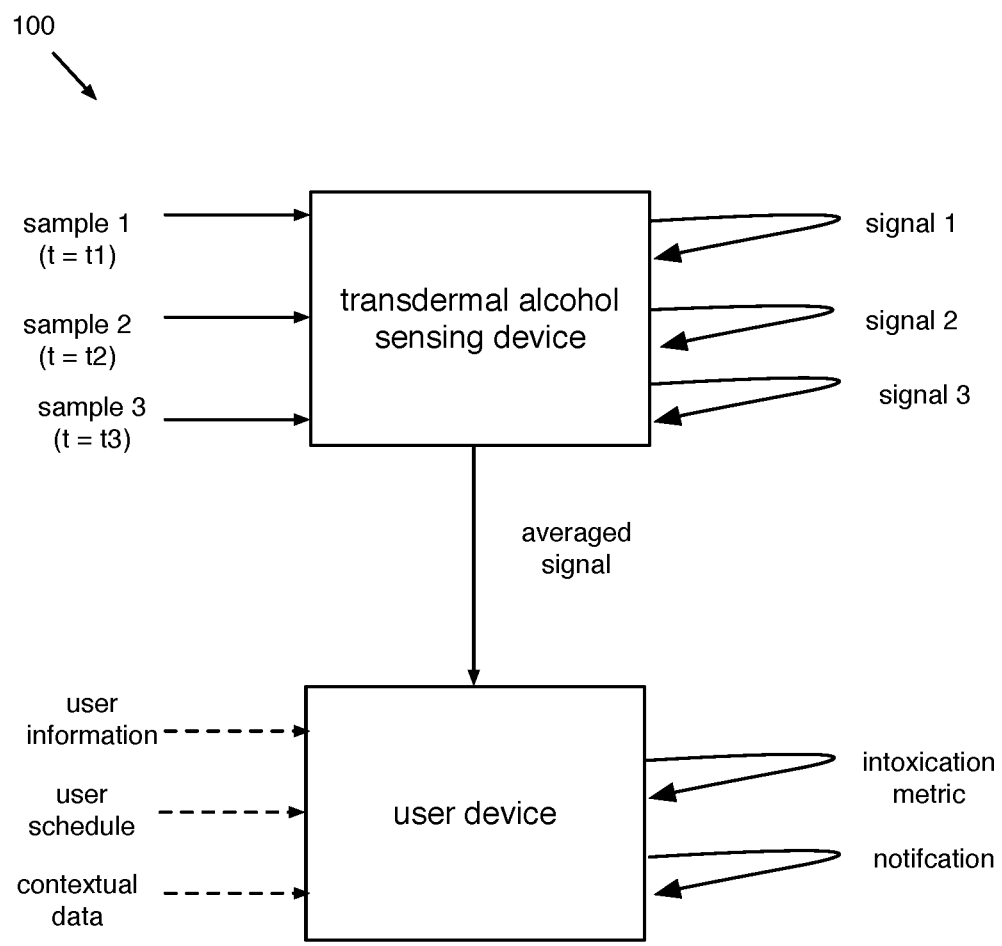
FIG. 12 depicts an example implementation of the method.

In some examples, the system 200 periodically syncs with a secondary device, such as a user device 260, where the secondary device is configured for any or all of: receiving and processing a signal from the system (e.g., a signal based on sensor measurements, based on supplementary sensor measurements, etc.), receiving and processing an electrical signal from a sensor (e.g., at a wristband device), receiving and processing an intoxication parameter, providing one or more notifications to a user, receiving user input, or any other suitable process. In a specific example, an averaged electrical signal is received from a sensor at a client application executing on the user device (e.g., as shown in FIG. 12).

Examples of the user device 260 include a tablet, smartphone, mobile phone, laptop, watch, wearable device (e.g., glasses), or any other suitable user device. The user device can include power storage (e.g., a battery), processing systems (e.g., CPU, GPU, memory, etc.), user outputs (e.g., display, speaker, vibration mechanism, etc.), user inputs (e.g., a keyboard, touchscreen, microphone, etc.), a location system (e.g., a GPS system), sensors (e.g., optical sensors, such as light sensors and cameras, orientation sensors, such as accelerometers, gyroscopes, and altimeters, audio sensors, such as microphones, etc.), data communication system (e.g., a WiFi transceiver(s), Bluetooth transceiver(s), cellular transceiver(s), etc.), or any other suitable component.

4. Method

As shown in FIG. 1, an embodiment of a method 100 for intoxication monitoring includes: receiving a set of samples from a body region of a user using a transdermal alcohol sensing device S110; generating an intoxication metric based on the set of samples S120; and providing a notification to the user based on the intoxication metric S130. The method 100 can additionally or alternatively include: modifying operation of the transdermal alcohol sensing device based on the intoxication metric S140; determining contextual data S150; maintaining a hydration level of the transdermal alcohol sensing device; and any other suitable processes.

4.1 Method: Receiving a Set of Samples from a Body Region of a User S110

Block S110 includes: receiving a set of samples from a body region of a user. Block S110 functions to obtain biological samples from a user that contain material that can be analyzed to determine an intoxication metric of the user. Block S110 is preferably performed using a wearable transdermal alcohol sensing device, such as the system 200 described above, but can additionally or alternatively be performed using a breathalyzer, a patch attached to a user by adhesive, and/or any other suitable alcohol sensing device.

The body region of the user preferably includes a wrist region (e.g., palm-side skin surface below hand, skin surface below hand opposing palm, skin surface opposing a watch face, skin surface beneath a watch face, etc.), but can additionally or alternatively include an arm region (e.g., shoulder region, upper arm skin surface, lower arm skin surface, etc.), leg region, torso region, head region (e.g., mouth region, forehead skin surface, neck skin surface, earlobe, etc.), or any other suitable region. For variations involving transdermal alcohol sensing, the body region is selected based on a perspiration level (e.g., does not experience excessive perspiration, is not too dry, etc.) of the body region. In some variations, for instance, regions of excessive perspiration (e.g., armpit) are avoided. Additionally or alternatively, the body region can be selected to avoid oily regions (e.g., avoid a sebaceous gland, etc.), excessive hair, or otherwise be selected in any other suitable way. In one variation, for instance, a bottom wrist region (e.g., adjacent to the palm of the hand) is chosen over an opposing top wrist region because the bottom wrist region experiences higher yet controlled perspiration, as well closer proximity to the bloodstream and better access to the skin.

Block S110 is preferably performed during a time window, and thus the set of samples is preferably a time-series of samples collected sequentially within the time window. The time window preferably includes a drinking session, but can additionally or alternatively include multiple drinking sessions, non-drinking time periods, pre-drinking time periods, post-drinking time periods, and any other suitable time periods. The time window is preferably continuous, but in alternative variations of Block S110 the time window can be discontinuous.

The time-series of samples is preferably taken at a predetermined regular frequency (e.g., 1 sample every second, 1 sample every 20 seconds, 1 sample every minute, 1 sample between every 1 second and every 20 minutes, less than 1 sample every 20 minutes, greater than 1 sample every minute, etc.). Additionally or alternatively, the frequency of sampling can be dynamic, adjustable, determined based on an intoxication level of the user (e.g., most recent TAC value, most recent BAC value, slope of intoxication curve, etc.), determined based on an environmental parameter (e.g., temperature, humidity, etc.), determined based on contextual or historical data (e.g., user intoxication history, user schedule, fitness activity, user profile, etc.), periodically updated (e.g., based on a software update of a client application executing on a user device), or otherwise determined. In a specific example, the frequency at which the time-series of samples is taken is based on an intoxication level of the user, such that when the user has a relatively high level of intoxication (and/or a rapidly increasing level of intoxication), samples are taken more frequently than when the user has a relatively low level of intoxication. In determining that the user has reached sobriety, for instance, S110 can optionally include stopping sample collection, turning off the sampling device, or performing any other suitable function.

One or more sampling parameters (e.g., frequency, timing, etc.) can additionally or alternatively be determined based on a particular application or goal (e.g., consumer use, criminal monitoring, pharmaceutical testing, etc.) for alcohol monitoring. Samples may be taken more frequently (e.g., every second) for pharmaceutical testing, for instance, than routine remote alcohol monitoring (e.g., 4 times per day).

In a first variation, S110 includes receiving a biological sample (e.g., ethanol vapor) transdermally from a transdermal alcohol sensing device. In preferred examples of this variation, a time series of transdermal samples are received regularly at the transdermal alcohol sensing device (e.g., at an inlet defined by the housing) from the user (e.g., wrist region of the user, arm region of the user, etc.), while the device is in an active sensing state (e.g., "on" state). The active sensing state can be initiated by any suitable triggers, such as—but not limited to—detection that the transdermal alcohol sensing device has been placed on the user, initiation of the "on" state by the user (e.g., upon pressing a power button of the housing), based on a calendar, based on a clock, based on a predetermined schedule, randomly, or based on any other suitable trigger. In alternative examples, a single sample is taken, a set of samples are taken at irregular intervals, or samples are otherwise taken.

In a second variation, multiple types of biological samples (e.g., transdermal skin samples and breath samples) are taken from a user (e.g., from the same body region, from different body regions, from the same alcohol sensing device, from different alcohol sensing devices, etc.), which can function, for instance, to determine a correlation function of the method (e.g., TAC to BAC conversion, BAC to time-to-sober conversion, etc.), to account for a limitation of a first type of biological sample with a second type of biological sample (e.g., account for lag of transdermal alcohol response with breath samples for an initial of period of time), otherwise supplement alcohol data determined from the samples, or perform any other suitable function. In a specific example, transdermal samples are taken from a user with a transdermal alcohol sensing device contemporaneously (e.g., at the same time, during an overlapping time interval, with a temporal separation of between 0 seconds and 1 hour, etc.) with breath samples taken from the user at a breathalyzer. The paired transdermal and breath samples are then used to determine and/or refine a correlation function for converting TAC values into BAC values. In a second specific example, the system can be calibrated for a given user by taking TAC values when the user is alcohol-free (e.g., as verified using a breathalyzer, as stated by the user, etc.), and by taking TAC values (and/or corresponding BAC values) at predetermined time intervals after the user has been dosed with a known amount of alcoholic beverage over a predetermined time period (e.g., 750 ml of beer in an hour). In a third specific example, one or more of the correlation functions can optionally identify environmental alcohol based on: the curve slope (e.g., wherein the slope is steeper than the slope due to ingested alcohol), the curve spread (e.g., wherein the spread is narrower than that for ingested alcohol), or otherwise determined.

In a third variation, multiple different indicators (e.g., chemicals, precursor chemicals, proteins, secretions, etc.) are collected and assessed from a single alcohol sensing device (e.g., transdermal alcohol sensing device, etc.). This can function to more accurately predict a future intoxication value, minimize lag in determining a TAC value, or perform any other suitable function. In one example, for instance, the method includes collecting transdermal oxygen at a transdermal alcohol sensing device, which can be used to detect and/or predict an intoxication level of the user (e.g., current intoxication, future intoxication, peak intoxication, etc.) earlier than the primary indicator (e.g., ethanol vapor). In this example, the method can optionally preferentially use TAC values determined from insensible perspiration measurements to determine BAC values after a predetermined time period (e.g., corresponding to insensible perspiration delay; such as 30 minutes, 45 minutes, 60 minutes, a period of time specific to the user or the user parameters, etc.). However, a combination of measurements can be otherwise cooperatively used to refine or serially determine the BAC measurement. Alternatively, any number and type of indicators can be collected at any single device or set of multiple devices.

4.2 Method: Generating an Intoxication Metric Based on the Set of Samples S120

Block S120 includes: generating an intoxication metric based on the set of samples. Block S120 functions to determine a parameter of interest, related to the intoxication of the user, using the received samples. Block S120 preferably functions to quantitatively assess an intoxication level of a user, which can optionally further function to trigger any number of notifications (e.g., to the user, to a monitoring agency, to another entity, etc.) or actions (e.g., automatically ordering a ride share vehicle for an intoxicated user). Additionally or alternatively, Block S120 can function to qualitatively assess an intoxication level of a user (e.g., track general progress of a user), share an intoxication level of a user (e.g., through social media, with an employer, etc.), or perform any other suitable function.

Block S120 is preferably performed at a processing system outside of the alcohol sensing device (e.g., transdermal alcohol sensing device, breathalyzer, etc.), such as a processing system associated with any or all of: a user device (e.g., processing system onboard the user device), client application executing on a user device, remote server, local server, or any other suitable location. Additionally or alternatively, any or all of Block S120 can be performed at a processing system onboard the alcohol sensing device.

The intoxication metric (e.g., as measured in grams of alcohol per deciliter of blood [g/dL], milligrams of alcohol per deciliter of blood [mg/dL], grams of alcohol per 210 liters of breath, etc.) can include a blood alcohol content (BAC) value, a transdermal alcohol content (TAC) value, a breath alcohol concentration (BrAC) value, a qualitative indicator of intoxication (e.g., wording such as "you're drunk", "you're tipsy", "you're stone cold sober", etc.), a binary metric (e.g., a go/no-go indicator based on a threshold parameter value), a timing metric (e.g., time until sober, time until peak, time until it's okay to drive, etc.), or any other suitable metric. The intoxication metric is preferably determined based on a signal (e.g., electrical signal) determined at the sensor based on the sample, but can additionally or alternatively be determined based directly on the sample, additional data from a supplementary sensor of the system, or any other suitable data.

The intoxication metric can additionally or alternatively include a parameter related to an intoxication curve (e.g., TAC curve, BAC curve, etc.) or function (e.g., constructed from a time series of intoxication metrics, predicted based on a set of intoxication metrics, predicted based on theory, etc.), such as—but not limited to—a slope, peak, span, average value, median value, area under the curve, the temporal proximity of the curve relative to adjacent curves (e.g., inter-peak distance), correlation with curve parameters for auxiliary compounds (e.g., sampled contemporaneously with the primary compound), or any other suitable parameter. Examples of auxiliary compounds (e.g., associated with intoxication) can include: transdermal oxygen, carbon dioxide, In an example, for instance, S120 includes determining a slope of an intoxication curve (e.g., TAC curve), which can effectively indicate a rate of drinking, wherein when the slope surpasses a predetermined threshold steepness, a trigger is initiated (e.g., notification to mobile phone to warn user, notification with instructions to stop drinking, suspension of payment through a mobile payment application, etc.).

Block S120 can optionally include determining a BAC value based on a TAC value. This variation preferably includes determining the BAC value based on a set of one or more predetermined correlation functions (e.g., retrieved from a database, stored at a processing unit of the alcohol monitoring device, etc.) that relates measured TAC values (and/or auxiliary compound measurements) to corresponding BAC values. However, this variation can additionally or alternatively include determining a correlation function in real time (e.g., based on simultaneously measured signals corresponding to BAC and TAC values) and determining the BAC value based on the correlation function determined in real time, and otherwise suitably determining the BAC value with or without a correlation function.

Each of the set of correlation functions can be an equation (e.g., linear regression) with weighted variables (e.g., time to peak TAC, gender, etc.), be a neural network, decision trees, rule sets, or be any suitable function or method. This variation can additionally or alternatively include: determining the BAC based on implementing a learning-based model (e.g., a learning agent or neural network trained according to machine learning principles, wherein TAC values are inputs to the model and BAC values are outputs of the model, wherein the model can be trained on-line or off-line using supervised learning, unsupervised learning, reinforcement learning, deep learning, etc.); determining the BAC based on a set of rules that transform a TAC value into a corresponding BAC value; and/or any other suitable means for determining the BAC value based on the TAC value. The BAC determination model (e.g., correlation function, etc.) can be: generic to all users; specific to a user (e.g., based on the user's use history; user's parameters, such as gender or location, based on a user's sweat volume, etc.); specific to a user population (e.g., wherein the population can share a common user parameter, such as gender or geographic location); or be otherwise used for different users.

As such, the set of one or more correlation functions can be determined based on any number of factors specific to a user, specific to the general population, determined by theory, or otherwise characterized. A correlation function, such as one specific to a user, can be determined based on any or all of the following user body information: fat content, sweat or perspiration level (e.g., sweat measurements, hyperhidrosis indication, etc.), activity level (e.g., heart rate, resting heart rate, workout log, etc.), skin type (e.g., color, race, dryness, oiliness, etc.), hair (e.g., type, amount, coarseness, etc.), tattoos, age (e.g., to determine a level of wrinkling), height, weight, food intake, ethnicity, or any other suitable user parameter.

An amount of sweat (e.g., volume of sweat, overall volume of sweat produced by user, daily volume, average volume per time period, rate of perspiration, etc.) generated by a user or set of users can potentially be useful to incorporate into a correlation function. When using a transdermal alcohol sensing device to take a sample from a skin surface of a user, for instance, a volume of sweat collected from a user can be used to better approximate a TAC value, a predicted future intoxication value, a predicted time until sober, or any other suitable value. In a specific example, for instance, an inflated intoxication parameter (e.g., "too high" TAC value) could result from a user having a high level of perspiration—a correlation function could take that into account (e.g., predict a sooner time until sober than would be otherwise determined), be calibrated based on a sweat level, or be otherwise determined.

Additionally or alternatively, one or more correlation functions can be determined or adjusted (e.g., reweighted, corrected, newly selected, etc.) based on any suitable contextual (e.g., environmental) data (e.g., as determined by supplementary sensors of the alcohol sensing device, as determined by a sensor of a user device, etc.). These can include any or all of: temperature, humidity, location, or any other suitable parameter. A cold environment (e.g., below 50 degrees Fahrenheit [deg F.], between 30 and 70 deg F., between 0 and 30 deg F., etc.) could, for instance, cause the sensor to respond more slowly, which could in turn trigger any or all of: the system having a larger delay prior to taking measurements (e.g., to preserve battery life), a notification to the user instructing him to step inside to take measurements, an adjustment within the correlation function, or any other suitable outcome. A hot environment (e.g., above room temperature, above 70 deg F., above 90 deg F., between 80 deg F. and 110 deg F., etc.) could be used to predict a user sweat volume, trigger an adjustment within the correlation function, or result in any other suitable outcome.

Block S120 can optionally include determining a correlation function based on multiple sample types. A comparison between a set of TAC values and a set of BrAC values (which can, in some instances, more closely correlate with BAC) contemporaneously taken (e.g., with a breathalyzer) can be used, for instance, in the determination of a correlation function. In a specific example, a set of samples is taken from a transdermal alcohol sensing device contemporaneously with a set of BrAC samples taken at any of the systems described in U.S. application Ser. No. 15/979,220, filed 14 May 2018, U.S. application Ser. No. 15/882,825, filed 29 Jan. 2018, U.S. application Ser. No. 16/010,093, filed 15 Jun. 2018, U.S. application Ser. No. 15/205,876, filed 8 Jul. 2016, and U.S. application Ser. No. 15/492,216, filed 20 Apr. 2017, which are each herein incorporated in its entirety by this reference.

Figure 8A:
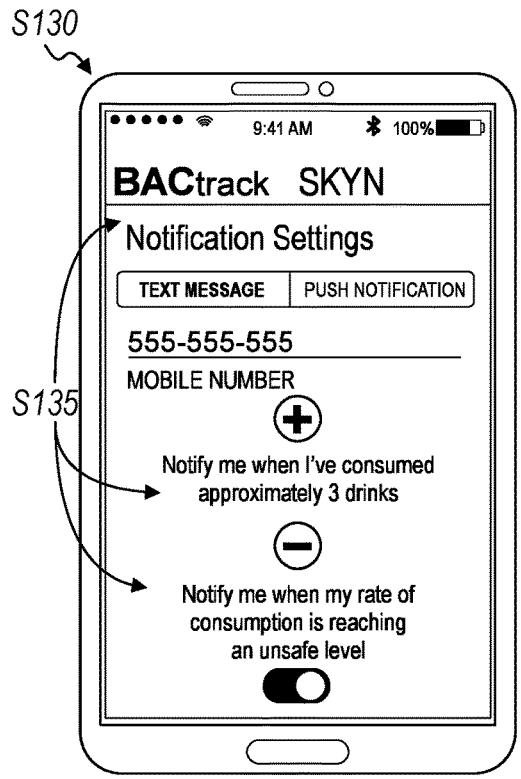
FIGS. 8A-8D depict example renderings in accordance with example implementations of portions of a method for transdermal alcohol monitoring.
Figure 8B:
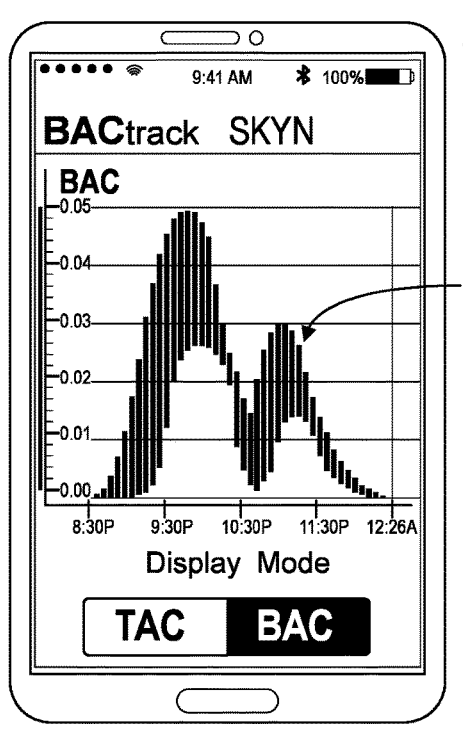
Figure 8C:
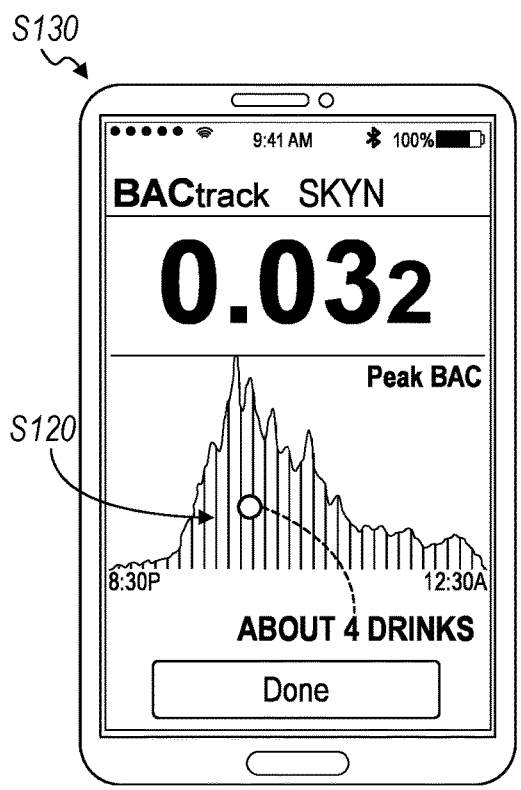

As shown by example in FIG. 8C, Block S120 can include integrating an area beneath a curve of values associated with the set of samples to generate an integrated value (e.g., representing total alcohol consumed during the time period spanned by the set of samples). The integrated value can represent the total alcohol consumed, which can be represented as a number of drinks (e.g., 3.6 drinks, about 4 drinks, etc.), a qualitative description (e.g., a lot, a little, too much, almost none, a safe level, an unsafe level, etc.), a quantitative description (e.g., thirteen ounces, one pint, etc.), and in any other suitable representation. In examples, one drink can be specified as a standard drink, equivalent and/or substantially equivalent to 12 ounces of beer having a 5% alcohol content, 5 ounces of wine having a 12% alcohol content, 1.5 ounces of liquor having a 40% alcohol content, and/or the like. In other examples, one drink can be specified as a single beverage, wherein instances of a single beverage can include various alcohol contents (e.g., a light beer having a 3% alcohol content, a craft beer having a 10% alcohol content, etc.). In further examples, Block S120 can include computing an equivalent number of standard drinks (e.g., as defined above) for the number of actual beverages (e.g., of various alcohol contents) consumed based on the set of samples.

Block S120 can additionally or alternatively include one or more signal processing processes applied to an intoxication curve, which can function to identify specific features and patterns of the user's drinking, as represented in the details of the intoxication curve. A convolution process (e.g., convolution of peaks), for instance, can be applied to an intoxication curve, which can enable the determination or approximation of the times at which the user consumed a beverage, the type of beverage, and/or any other suitable information. In an example, a convolution analysis of an intoxication curve resulting in the determination that three sudden spikes occurred during the drinking session, which corresponds to the user taking three shots of alcohol in a row. Based on the steepness of the curves (e.g., spikes), it could be determined, for instance, that the user instead sipped a cocktail over a longer period of time. Additionally or alternatively, the type of beverage can be determined from one or more intoxication curve parameters, wherein the parameter values (or derivative features thereof, such as patterns) can be correlated or otherwise associated with different beverage types. Additionally or alternatively, Block S120 can include any other suitable processing of an intoxication curve.

Block S120 can additionally or alternatively include determining a recovery rate from alcohol (rate at which alcohol is processed by the liver and eliminated from the body), which can be used to initiate a trigger (e.g., notification to user to stop drinking), update a user schedule (e.g., suggest a last drink time in light of a proposed driving time), or be used for any other suitable outcome. In the event that the recovery rate is higher than a predetermined threshold (e.g., 0.015 g/100 mL/hr), a notification can be provided that the user is classified as an alcoholic or in danger of becoming an alcoholic.

Block S120 can optionally include any suitable type of data transmission, data processing, and data storage. To preserve memory (e.g., onboard an alcohol sensing device), for instance, Block S120 can include taking an average or otherwise aggregating a set of sample signals (e.g., every 20 seconds, every 20 collected sample signals, between every 2 and every 1000 sample signals, etc.) and storing only the average/aggregated value. This can be performed at regular time intervals (e.g., every 20 seconds, between every 1 second and every hour, more than once per second, less than once per hour, etc.), at irregular time intervals (e.g., dynamically updated, random, etc.), in response to a trigger (e.g., when alcohol sensing device is in close proximity with a user device), or at any other suitable time. Additionally or alternatively, Block S120 can include any or all of: storing a subset of samples (e.g., each sample at a predetermined interval, every third sample, random subset, etc.), storing all samples, storing a median value of samples, storing minimum values, maximum values, or any other suitable sample signals.

In variations of the method including a user device in communication with the alcohol sensing device, Block S120 can include periodically (e.g., at predetermined intervals of time, after a predetermined number of samples have been collected, etc.), syncing the alcohol sensing device and the user device (e.g., a foreground client application executing on the user device, a background client application executing on the user device, etc.). This can function to preserve battery life onboard the alcohol sensing device while still regularly communicating signals to the user device for processing. Alternatively, the alcohol sensing device can be continuously synced with a user device, never synced, synced in response to a trigger (e.g., prompting by the user, prompting from the user device, based on a charge level of the alcohol sensing device, when the wristband device and user device are in close proximity, etc.). In these variations, Block S120 can additionally or alternatively include removing (e.g., deleting, not storing, etc.) redundant parameter values (e.g., redundant signal values, redundant intoxication metrics, etc.). In an example, for instance, Block S120 includes comparing a set of signal values (e.g., averaged values) received from the alcohol sensing device (e.g., received contemporaneously, sequentially, at different points in time, etc.) and not storing (or removing if already stored) redundant values from memory associated with the user device. Block S120 can further additionally or alternatively include pushing data (e.g., intoxication metrics, signal values, etc.) to a server (e.g., remote server, cloud-based server, etc.) or other remote system (e.g., user device 260) for any or all of: further processing, association with user data stored at the server, storage of data, or any other suitable process.

In a first variation, Block S120 includes estimating a peak intoxication metric reached during a drinking session. Estimating the peak intoxication metric can include estimating the peak BAC value, the peak TAC value, and the peak of any other suitable value related to intoxication. Estimating the peak can include interpolating, extrapolating, modeling, directly measuring, and/or any other suitable technique for determining the peak value. For example, Block S120 can include interpolating between values in the set of samples collected over the time period of the drinking session to evaluate a continuous curve of BAC or TAC values in which the peak value resides. Interpolating in accordance with this and other examples can be performed according to a linear interpolation model, a quadratic interpolation model, a piecewise cubic interpolation model, a nonlinear model for intoxication metric dynamics over time, and any other suitable technique for interpolation.

In a second variation, Block S120 includes receiving a set (e.g., 20, greater than 2, between 2 and 1000, greater than 1000, etc.) of electrical signals (e.g., current values) from a sensor of an alcohol sensing device, the set of electrical signals determined based on a set of samples; averaging the values of the set of signals to determine an averaged value; syncing the alcohol sensing device with a user device after receiving the set of signals; transmitting the averaged value to the user device; checking for redundancy between the averaged value and previously received averaged values; eliminating redundant values; determining an intoxication metric based the averaged value; and updating an intoxication curve.

4.3 Method: Providing a Notification to the User Based on the Intoxication Metric S130

Block S130 includes: providing a notification to the user based on the intoxication metric. Block S130 functions to inform the user of the user's level of intoxication and/or consequential information pursuant to the user's level of intoxication. Rendering information can be considered as providing a notification irrespective of whether the notification is in response to a trigger or otherwise suitably generated (e.g., persistent notification and rendering data at a client application executing on a mobile device of the user can be considered substantially equivalent).

The notification can include any or all of: an audio notification (e.g., through a speaker of a user device, through a speaker of the alcohol sensing device, etc.), visual notification (e.g., as shown in FIGS. 9A-9D, through a light emitter, through a display, an image provided at a display, a graphic provided at a display, etc.), cellular notification (e.g., call to another individual through a mobile phone of the user communicatively coupled to the system), text, web alert, push notification (e.g., iOS push notification, Android push notification, etc.), tactile notification (e.g., at a vibration motor of the system, at a haptic stimulus of a watch that the system is retrofitted to, at a user device communicatively coupled to the system, etc.), or any other suitable notification. A visual notification can include one or more graphical representations of a set of one or more intoxication metrics (e.g., an intoxication metric curve), a progress bar (e.g., indicating number of drinks consumed, percentage of peak intoxication reached, percentage of time left until sober, etc.), or any other suitable visual. In an example, the visual notification can include extrapolated (e.g., nonlinear extrapolation) and or predicted regions of an intoxication curve (e.g., a curve with a predicted peak based on historical data for user). Additionally or alternatively, the visual input can include and/or be based on a current slope of an intoxication curve, a user input (e.g., number of drinks planned to be consumed, etc.), or any other suitable information. In another example, a visual notification in the form of a color indication, such as the activation of a light emitter (e.g., green light emitter for sober and red light emitter for intoxication above legal limit) can be provided. The light emitter can be a point source, a light pipe (e.g., forming the wristband of the system 200), a display, or any other suitable light emitter. Providing color indications indicating "drunkenness" (binary drunkenness or degree of drunkenness) at a user wristband, for instance, could be useful in an event (e.g., concert) setting, where all the attendees have wristbands indicating their intoxication.

The notification (e.g., type, timing, etc.) is preferably determined based on one or more intoxication metrics, but can additionally or alternatively be determined based on any or all of: user historical data (e.g., previous intoxication peak, duration of time user spends at a particular bar, etc.), behavioral data, biological data (e.g., notification requesting that user wipe of off sweat prior to subsequent sampling, etc.), or any other suitable data.

The notification is preferably provided to the user but can additionally or alternatively be provided to another individual (e.g., probation officer, family member, monitoring account associated with the user account of the user, etc.), server (e.g., remote server), database, or any other suitable individual or notification.

Block S130 can include rending one or more notifications at a display of a user device (e.g., mobile device) associated with the user; the user device can, in variations, be the transdermal alcohol sensing device (e.g., a smartwatch including the TAC sensor and a display), a separate device (e.g., the user's smartphone, the user's laptop, etc.), a web page, and any other suitable device or location. Block S130 can additionally or alternatively include providing the notification without rendering the notification (e.g., via a text message, via a phone call, via an audio output, via a haptic output, etc.). In variations, Block S130 can include rendering any suitable information in relation to the intoxication metric and/or the set of samples indicative thereof at a display of a mobile device of the user, as shown by example in FIGS. 8A-8D.

Block S130 can additionally or alternatively include providing one or more notifications at the alcohol sensing device, such as through one or more light emitters, speakers, vibration motors, or any other suitable outputs.

Figure 6:
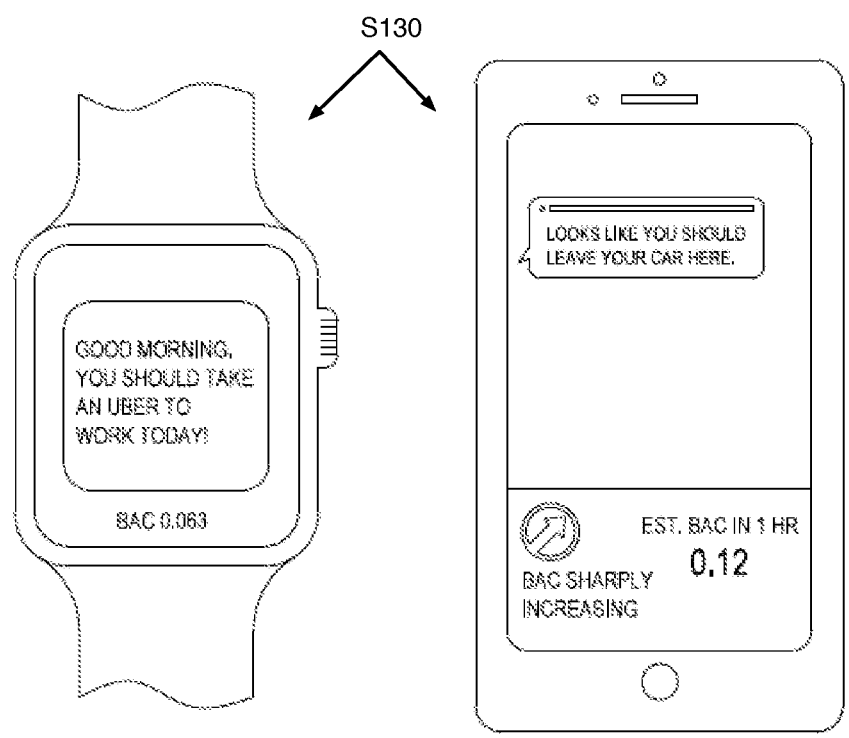
FIG. 6 depicts a schematic illustration of a portion of an example implementation of a method for transdermal alcohol monitoring.

Block S130 can include providing a plurality of notifications, at one or more mobile devices. The plurality of notifications can be provided independently and/or in conjunction; for example, as shown in FIG. 6, a first notification can be provided at a mobile phone of the user based on the rate of BAC increase, and a second notification can be provided at a wearable smart device of the user that includes a suggestion for the user to avoid operating a motor vehicle, wherein the first and second notifications are provided at distinct times on distinct devices, related to the same drinking session.

Block S130 can optionally include providing one or more notifications for the purposes of social applications; this can include, for instance, inviting contacts out for a night out upon determining that the user is drinking at a bar.

Figure 8D:
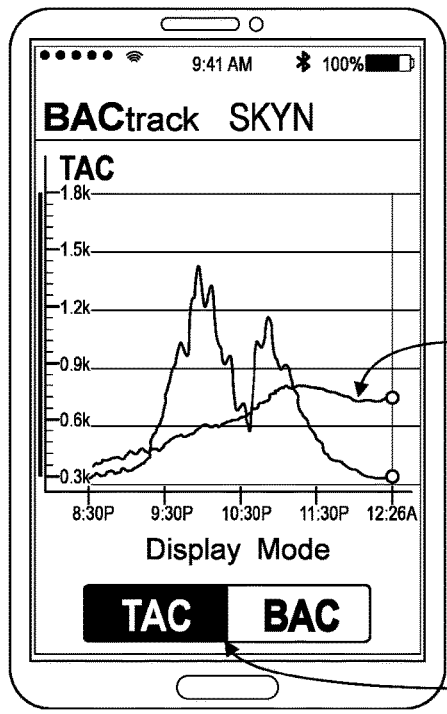
Figure 9A:
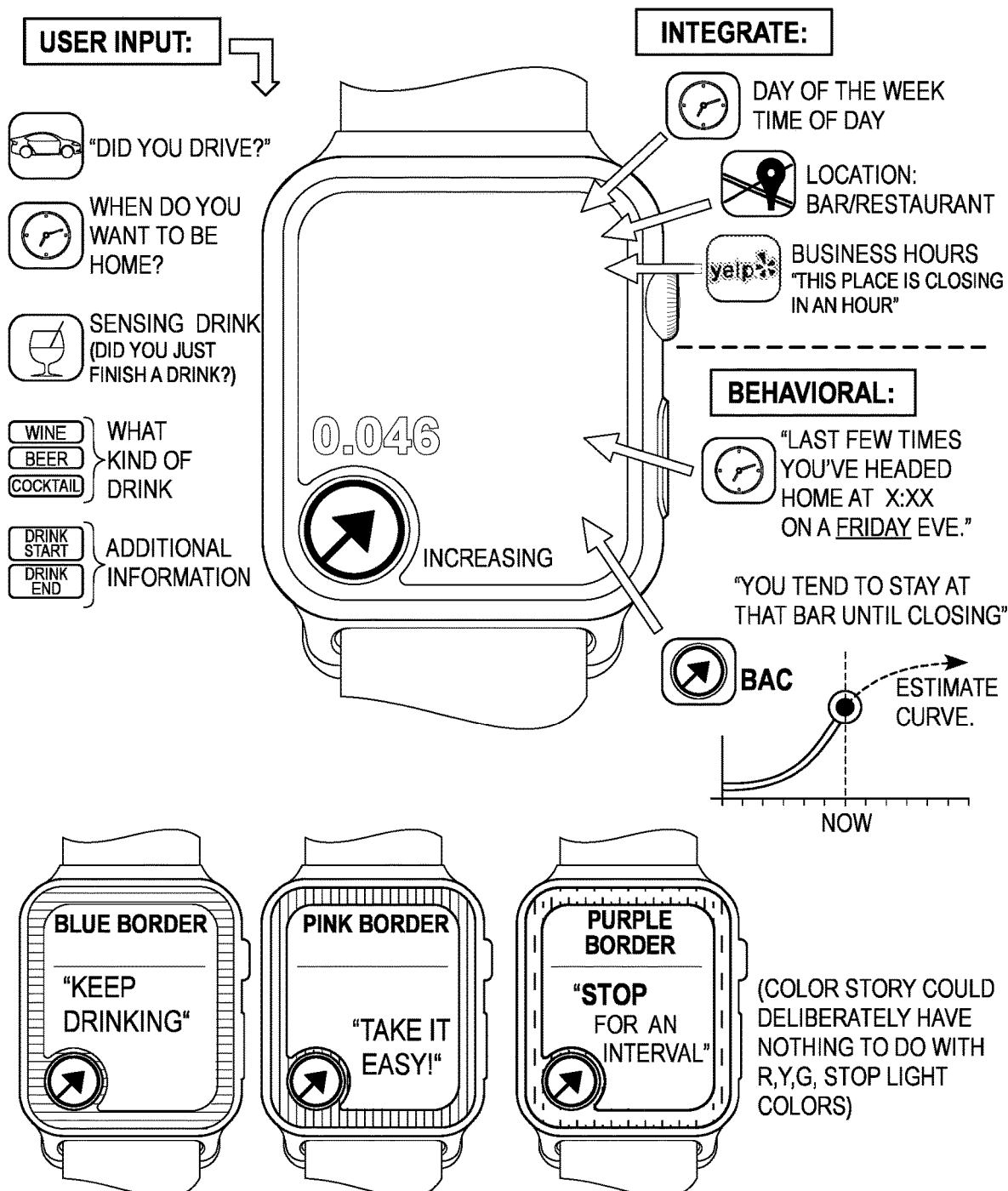
FIGS. 9A-9D depict example renderings of notifications provided at a display of a user device.
Figure 9B:
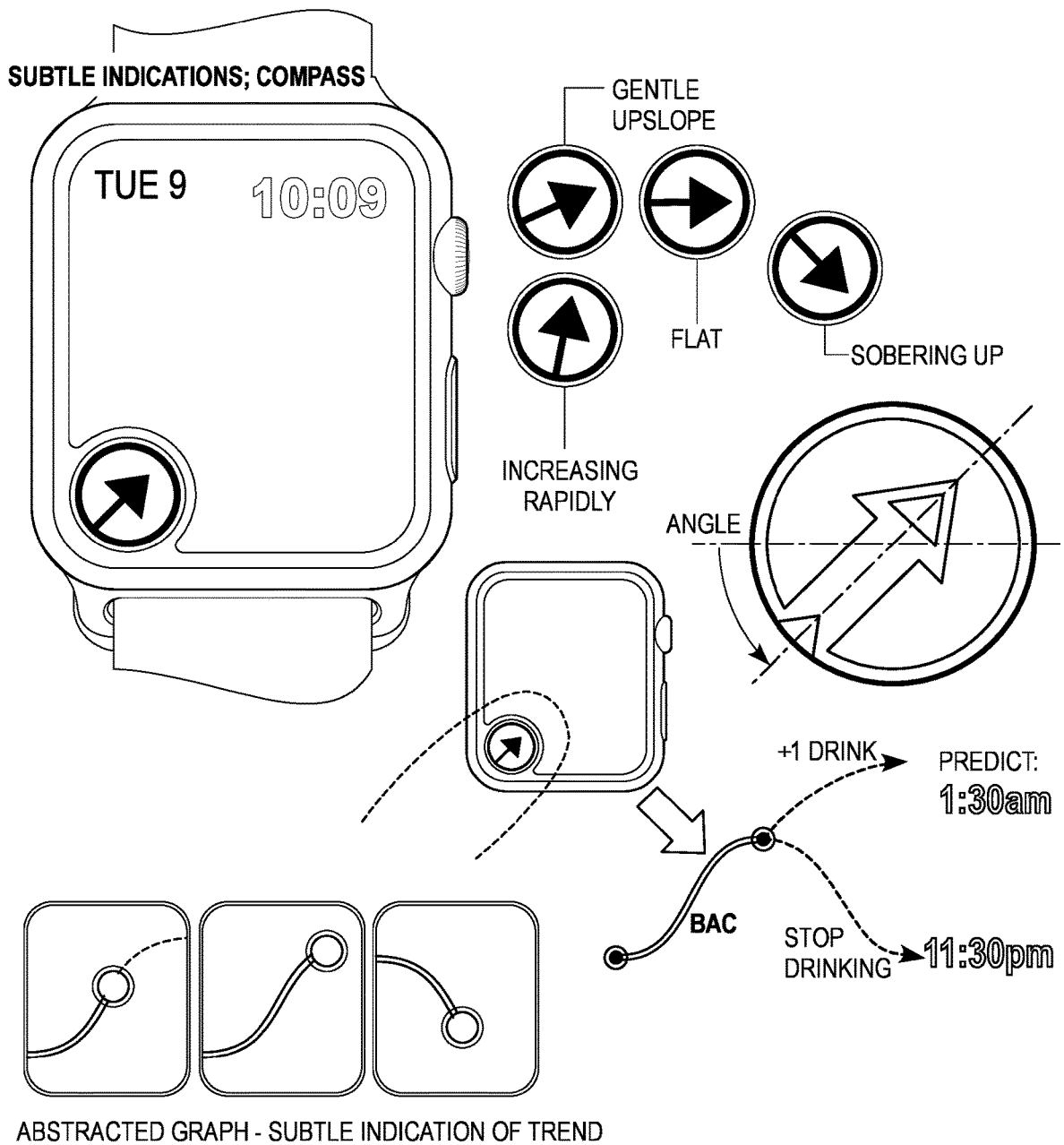
Figure 9C:
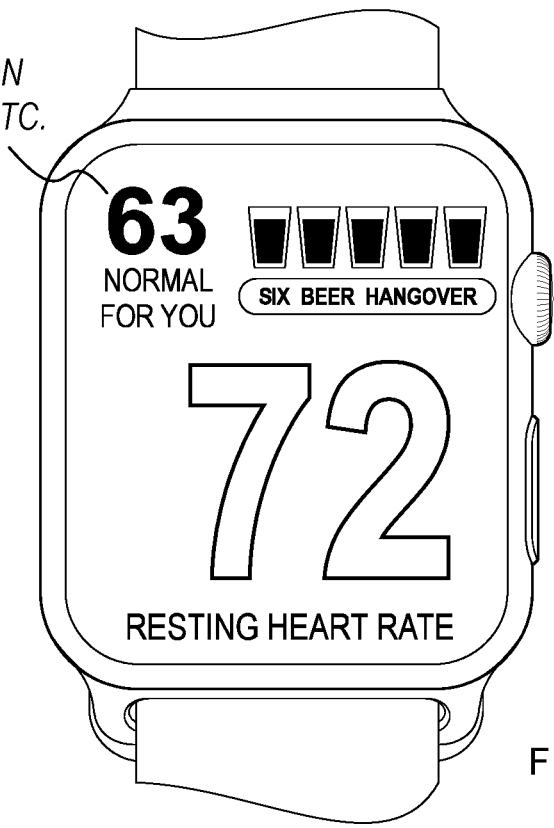
Figure 9D:

Block S130 can include rendering a time series of values selectable between a TAC display mode and a BAC display mode. For example, as shown in FIG. 8D, Block S130 can include rendering an option selector at a display of the mobile device that enables the user to switch between a TAC display mode and a BAC display mode.

In relation to Block S130, time series values can be rendered such that error bars (e.g., based on measurement error, sensitivity analyses, the measurement method or system, etc.) are rendered in conjunction with the measured values of TAC and/or determined values of BAC. For example, as shown in FIG. 8B, a curve of BAC values and associated symmetric error bars associated with each value can be displayed.

Block S130 can include providing a notification to the user based on contextual data (e.g., determined in Block S150 as described below). For example, Block S130 can include rendering a curve of skin temperature values versus time at a display of a mobile device of the user, as shown in FIG. 8D. In another example, Block S130 can include determining that the user is driving in a vehicle (e.g., based on GPS data from the user's phone), and provide a notification (e.g., a warning) to the user and/or another entity associated with the user based on BAC and/or TAC results determined from the user (e.g., at a transdermal alcohol sensing unit).

Block S130 can include providing notifications to a user through a client application executing on a user device in communication with an alcohol sensing device. The client application preferably can also receive one or more inputs from the user, as well as optionally interact with other client applications executing on the user device (e.g., scheduling applications, ride share applications, user information applications, weather applications, etc.). The integration of this client application with other client applications can function to trigger notifications on the other applications and/or receive notifications at the client application from the other applications. These other applications can be configured to include any or all of: time information (e.g., time of day, day of week, etc.), calendar information (e.g., general calendar information, user-specific calendar information, etc.), location information (e.g., GPS data, user location, name of bar at which user is located, etc.), information related to the user's location (e.g., bar's business hours, type of alcohol served, etc.), payment information (e.g., knowledge that user has purchased a particular drink), transportation information (e.g., through a ride-sharing application), or any other suitable information.

In one variation, S130 includes prompting a user to use a ride share application (e.g., through a notification at a ride share application, through a test message, by opening the ride share application, etc.), which can be initiated in response to any or all of: determining that a user has reached a predetermined intoxication threshold, determining that a time until sober is later than a bar closing time, or any other suitable information.

Block S130 can optionally provide notifications based on a schedule of a user (e.g., as indicated in a calendar application of the user, as input by the user into the client application, etc.). Additionally or alternatively, a user schedule can be updated based on the intoxication metric. Having access to a user schedule can function, for instance, to plan a user's night out, provide instructions to a user to enable them to follow their schedule (e.g., stop drinking now to be able to drive home at a predetermined time point, call a cab instead of driving home, wait an hour before your next drink to maintain a buzz and not reach a particular intoxication peak, drink a glass of water, etc.).

The notification can optionally be correlated with one or more health metrics of the user, such as—but not limited to—sleep quality (e.g., indicating that a user's drinking session has impacted or will impact the user's sleep quality), a hangover likelihood and/or predicted severity, a user weight change or overall weight, an exercise or workout (e.g., indicating when a user should perform a workout), overall nutrition, or other area of the user's health.

Block S130 can include Block S135, which includes receiving user input related to notification provision. Block S135 functions to receive input from the user that define the user's desired notification parameters. For example, as shown in FIG. 8A, Block S135 can include receiving a user preference that stipulates that a notification should be provided in accordance with Block S130 upon the detection of consumption by the user of a number of drinks exceeding a threshold (e.g., a threshold of three standard drinks). In a related example, also shown in FIG. 8A, Block S135 can include receiving a user preference that stipulates that a notification should be provided in accordance with Block S130 upon detection of a rate of consumption greater than a threshold rate (e.g., an unsafe rate, a rate of three drinks per half hour, etc.). Block S135 can additionally or alternatively include receiving a preference indicative of the type of notification that is desired, such as a text message, an automated phone call, a push notification, and the like. Block S135 can additionally or alternatively include receiving user input in the form of user contact information, such as a mobile phone number or other suitable contact information, that facilitates the provision of the notification(s) to the user. However, Block S135 can additionally or alternatively include receiving any suitable user input.

Figure 5:
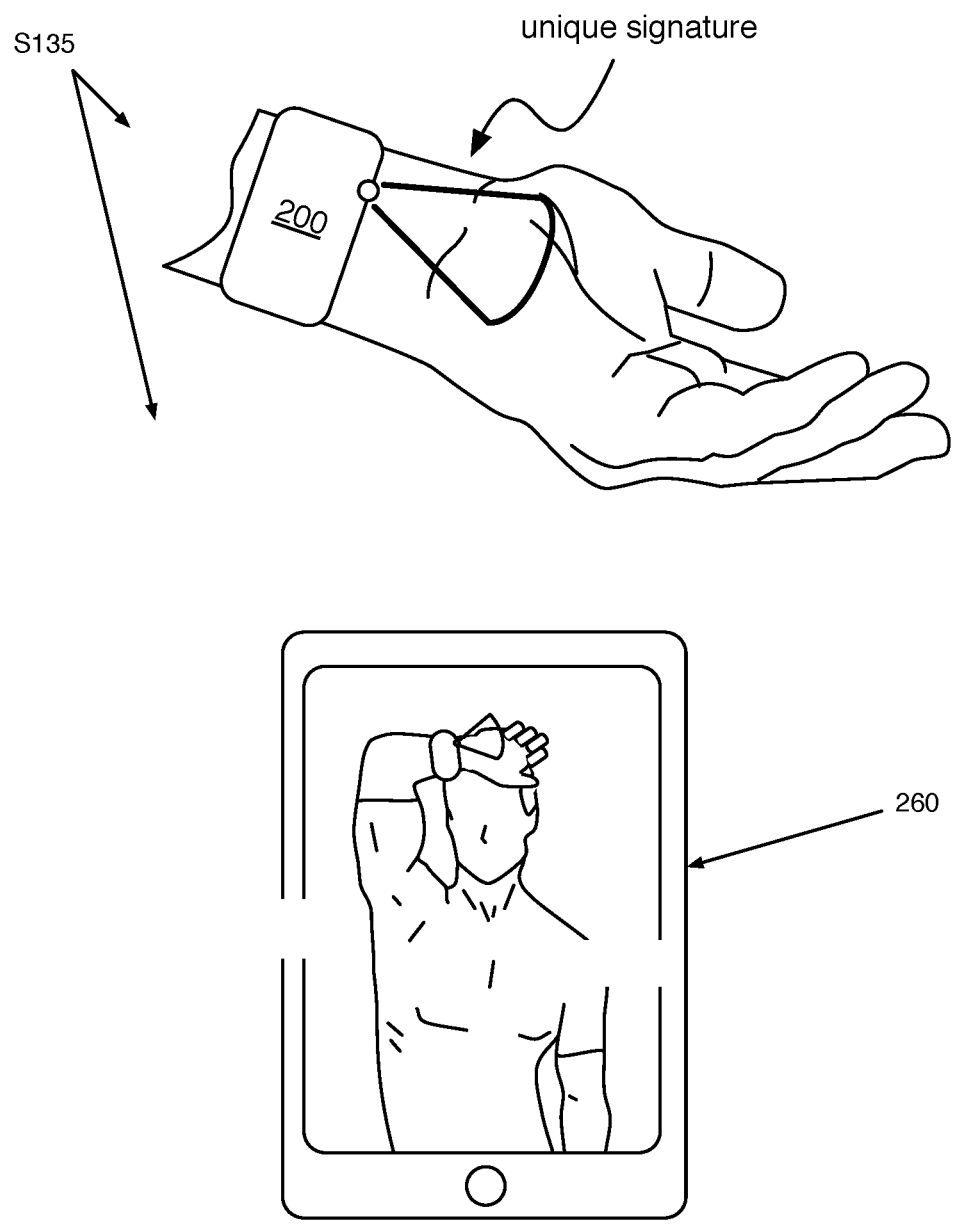
FIG. 5 depicts a schematic illustration of an example of a portion of a variation of a method for transdermal alcohol monitoring.

In a specific example, receiving user input in accordance with Block S135 includes receiving a unique signature emitted by the alcohol sensing device. The unique signature is preferably received by a second device (e.g., at a sensor of a mobile device associated with the user that is distinct from the alcohol sensing device as shown in FIG. 5), and functions to identify the device being used to receive the set of samples contemporaneously with receiving the set of samples (e.g., as an authentication mechanism).

Figure 7:
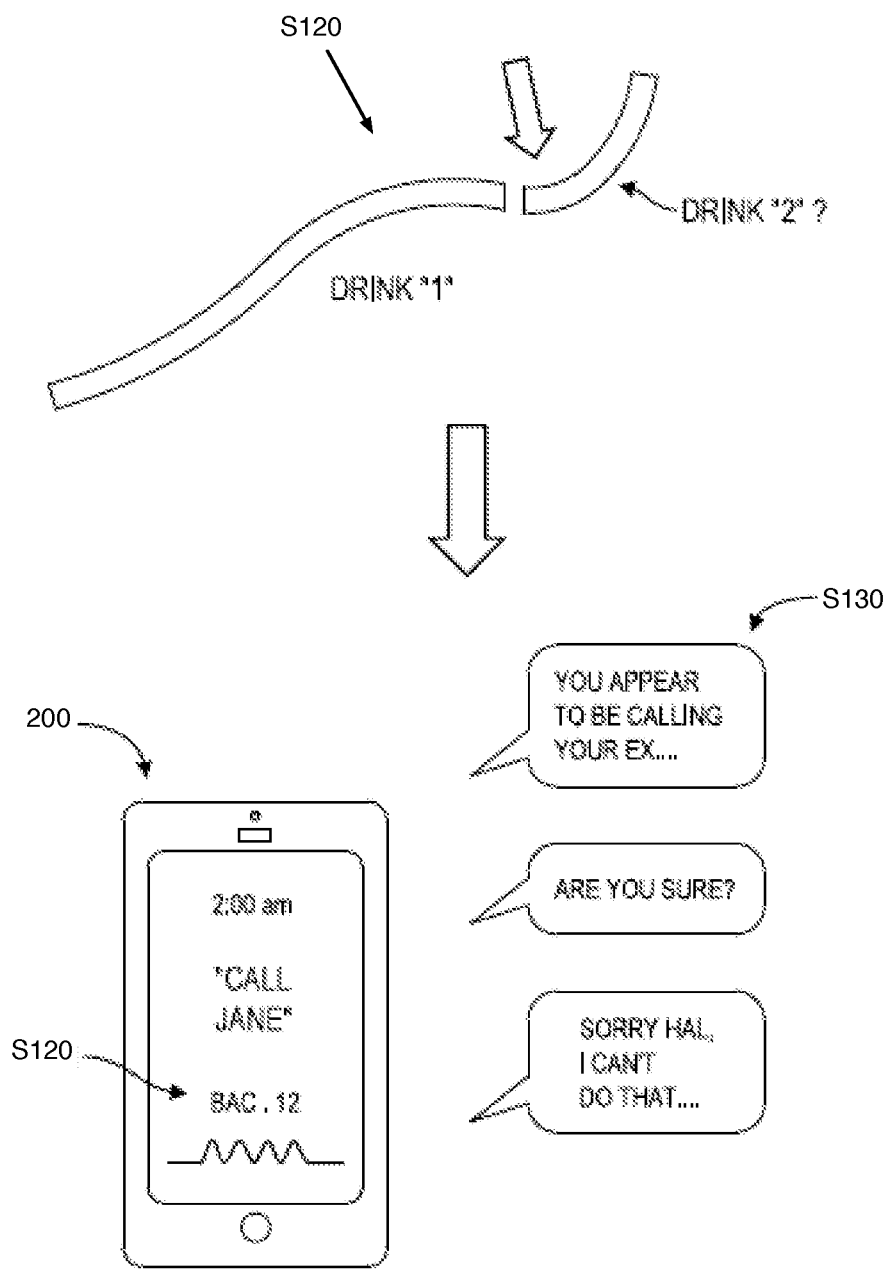
FIG. 7 depicts a flowchart schematic of a portion of an example implementation of a portion of a method for transdermal alcohol monitoring.

In another specific example, Block S135 includes receiving a block list of entities, and preventing contact of the entities on the block list (e.g., ex-partners, coworkers, etc.). Contact prevention is preferably performed in cases wherein the user's intoxication metric exceeds a threshold value (e.g., a BAC of 0.0, a TAC of 0.01, a BAC of 0.10, etc.), but can additionally or alternatively be performed based on alternative metrics (e.g., temporal metrics, including preventing contact between predetermined hours of the day according to a schedule) and/or combinations of alternative metrics and intoxication metrics. Preventing contact can include disabling features of the user's mobile device that facilitate contact (e.g., calling features, text messaging features, internet navigation features, etc.) in a general (e.g., globally limiting mobile device functionality) and/or specific (e.g., in relation to solely those entities on the block list) manner. Preventing contact can additionally or alternatively include providing a suggestion to the user that the user desist from contacting the entities on the block list (e.g., as shown in FIG. 7).

4.4 Method: Modifying Operation of the Transdermal Alcohol Sensing Device Based on the Intoxication Metric S140

The method can include Block S140, which includes: modifying operation of the transdermal alcohol sensing device based on the intoxication metric. Block S140 functions to optimize alcohol sensing device operation based on measured and/or derived data (e.g., the set of samples and/or the intoxication metric, respectively).

Figure 3:
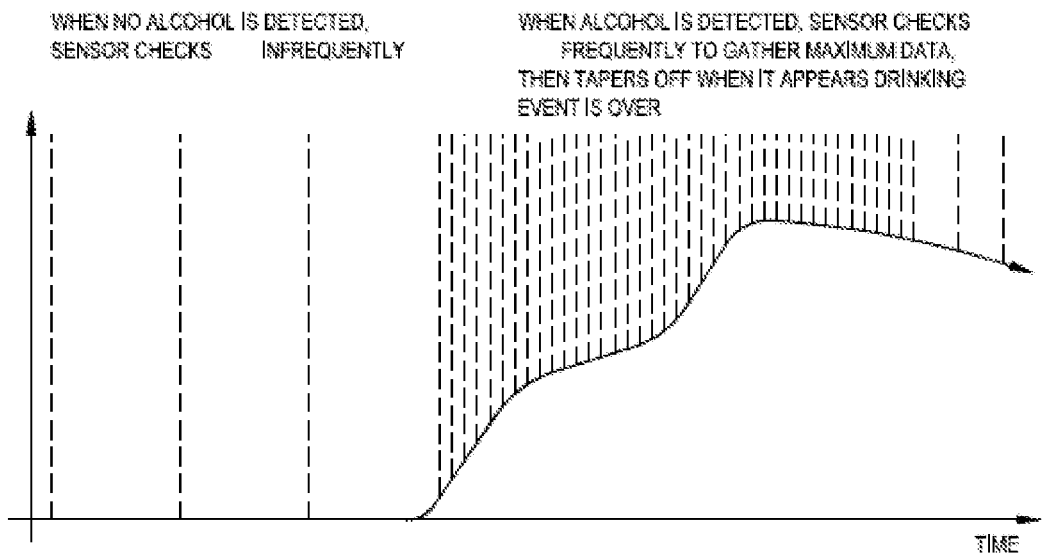
FIG. 3 depicts an example implementation of a portion of a method for transdermal alcohol monitoring.

As shown in FIG. 3, Block S140 can include controlling the sensor to collect data less frequently when frequent readings are not desired (e.g., when no alcohol is detected)

and/or controlling the sensor the sensor to collect data more frequently (e.g., at a maximum sampling rate, at an elevated sampling rate) when frequent readings are desired (e.g., when alcohol is detected), which can function to reduce power consumption, computing power consumption, data storage/bandwidth consumption, and the like.

4.5 Method: Determining Contextual Data S150

The method can include Block S150, which includes: determining contextual data. Block S150 functions to determine data that can be used to augment the determination of the intoxication metric (e.g., in accordance with Block S120). For example, Block S150 can include measuring skin temperature values at a contact temperature sensor of the transdermal alcohol monitoring device.

Block S150 can include determining correlations between alcohol consumption and other health metrics (e.g., sleep quality, weight, exercise, diet, heart rate, blood pressure, hangover symptoms, behavior characteristics, etc.) and presenting data about the other health metrics and/or the correlations to a user (e.g., at a user device, at the alcohol sensing system) determined as and/or by way of contextual data.

4.6 Method: Hydrating the Transdermal Alcohol Sensing Device

The method 100 can optionally include hydrating a transdermal alcohol sensing device, which functions to keep the sensor of the transdermal alcohol sensing device function properly (e.g., such that the sensor can properly adsorb the sample, to wash off prior sample residue, etc.). Hydrating can include any or all of: wetting a membrane of the sensor with a fluid (e.g., water), applying active humidification, active or passive application of a liquid to a membrane or surface of the sensor (e.g., through wicking, capillary action, pressure, vacuum, etc.), capping the sensor (e.g., at the inlet) in between uses, or any other process.

In one variation, hydrating includes moistening a membrane of the sensor at a predetermined interval of time (e.g., every two months).

Blocks of the method 100 can be repeated in order to build out a database of sensor data, in a similar manner as described above in relation to data aggregation. Furthermore, Blocks of the method 100 can be repeated over time for an individual user and/or multiple users, in order to generate models that describe longitudinal behavior (e.g., of a user's intoxication state) over time, as described in relation to the machine learning models and training data described above.

Furthermore, in relation to repetition of blocks of the method 100, each instance of sample provision can be performed without re-establishment of a baseline test result. For instance, if there is residual alcohol interacting with a sensor in association with sample provision and analysis, Blocks of the method 100 can be used to account for residual alcohol effects, such that the individual does not have to wait for an extended period of time between subsequent instances of sample provision.

However, the method 100 can include any other suitable blocks or steps, some embodiments, variations, and examples of which are described in in U.S. application Ser. No. 15/294,317 filed on 14 Oct. 2016, U.S. application Ser. No. 14/470,376 filed 27 Aug. 2014, U.S. application Ser. No. 14/602,919, and U.S. application Ser. No. 15/205,876, which are each incorporated herein in their entireties by this reference. For example, the system 200 can include an output (e.g., optical output, such as a light emitter or electronic display; audio output; etc.) operable to output a unique signature, and the method 100 can include acquiring sensor data including a photograph or video displaying the user wearing the system 200 and including the unique signature (e.g., in the photograph or video), an example of which is shown in FIG. 5.

The method 100 can additionally or alternatively include any other suitable blocks or steps configured to facilitate use of data to provide more dynamic and accurate information related to intoxication test results. Furthermore, as a person skilled in the art will recognize from the previous detailed description and from the figures and claims, modifications and changes can be made to the method 100 without departing from the scope of the method 100.

Figure 11A:
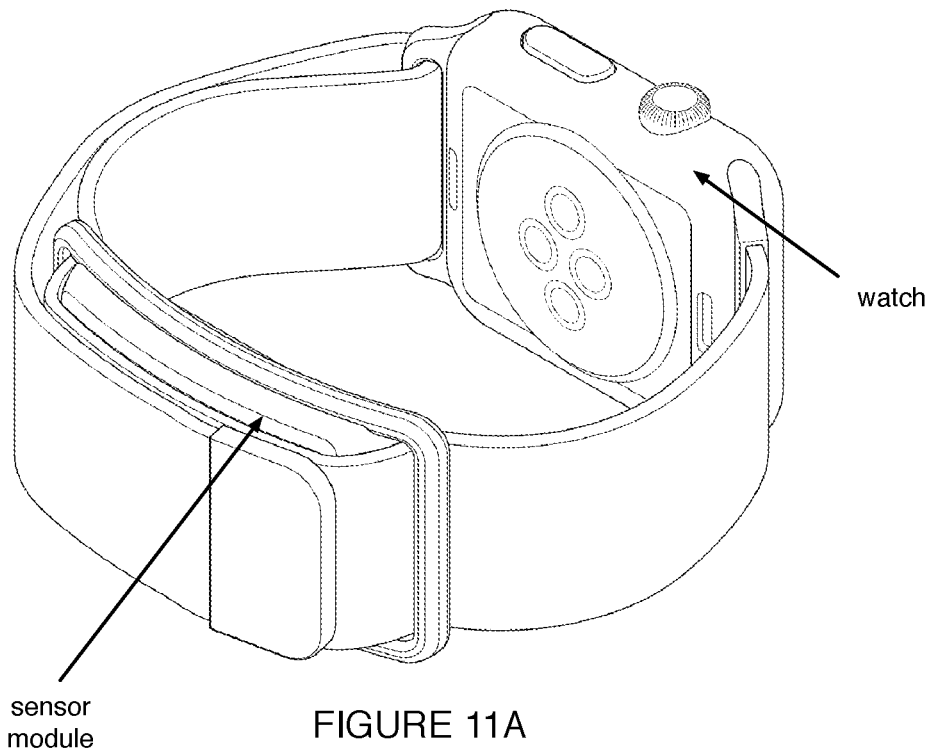
FIGS. 11A-11B depict an embodiment of the system.
Figure 11B:
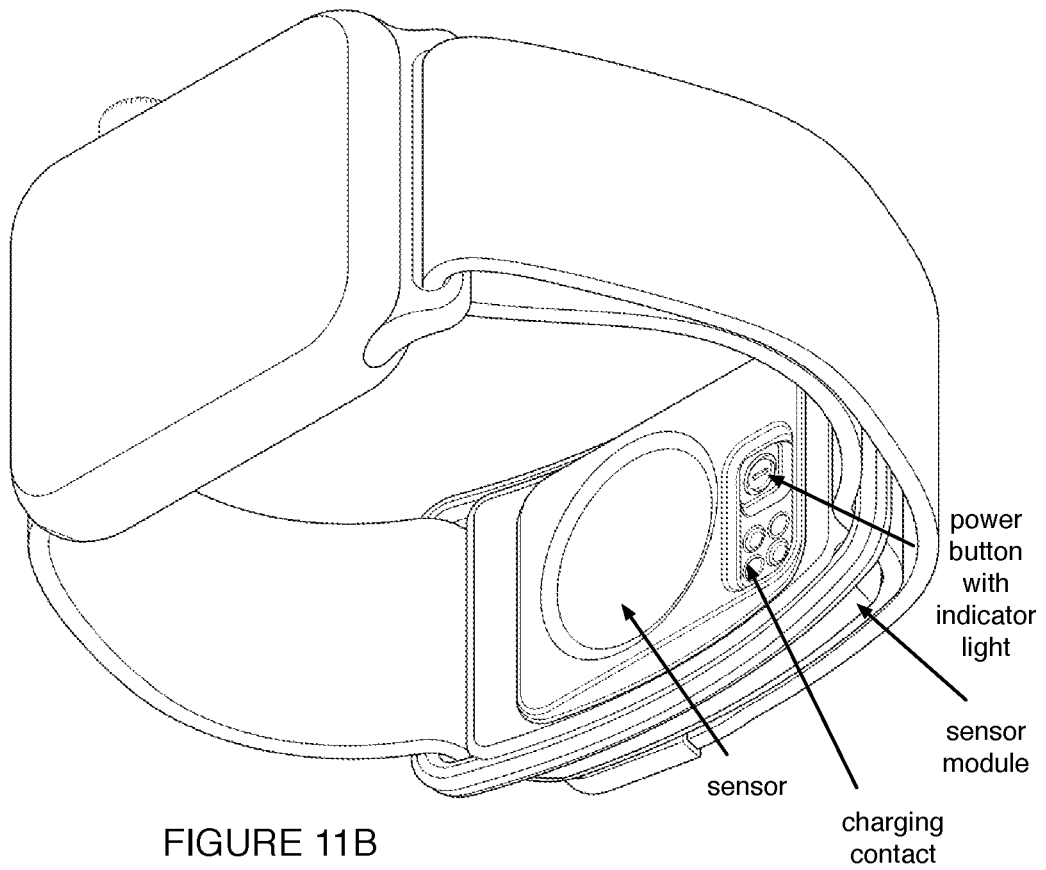

In one variation, the method 100 includes: receiving a set of ethanol samples from a user at an inlet of a transdermal wristband device (e.g., as shown in FIGS. 10A-10B, as shown in FIGS. 11A-11B, etc.); determining a set of electrical signals based on the set of ethanol samples at a sensor of the wristband device; storing the set of electrical signals at memory of the wristband device; determining an aggregated electrical signal (e.g., average electrical signal) from the set of electrical signal values; syncing the transdermal wristband device with a user device in communication with the transdermal wristband device; transmitting the aggregated value to the user device; determining a TAC value based on the aggregated value; and providing a notification based on the TAC value at a client application executing on the user device. The variation can additionally or alternatively include any other suitable processes performed in any suitable order.

The preferred embodiments include every combination and permutation of the various system components and the various method processes. Furthermore, various processes of the preferred method can be embodied and/or implemented at least in part as a machine configured to receive a computer-readable medium storing computer-readable instructions. The instructions are preferably executed by computer-executable components preferably integrated with the system and one or more portions of the electronics subsystem 150. The computer-readable medium can be stored on any suitable computer readable media such as RAMs, ROMs, flash memory, EEPROMs, optical devices (CD or DVD), hard drives, floppy drives, or any suitable device. The computer-executable component is preferably a general or application specific processing subsystem, but any suitable dedicated hardware device or hardware/firmware combination device can additionally or alternatively execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

We claim:

1. A method for monitoring intoxication of a user, the method comprising:
   at a transdermal alcohol sensing device coupled to a wrist region of the user:
      receiving a set of samples from a skin surface of the user;
      determining a set of signals at a sensor of the transdermal alcohol sensing device based on the set of samples;
      storing a value associated with the set of signals at memory associated with the transdermal alcohol sensing device;
      transitioning to a first operation mode, wherein in the first operation mode, the transdermal alcohol sensing device transmits the value to a client application executing on a user device;
   at the client application:
      receiving the value;
      determining a sweat parameter associated with the set of samples, wherein the sweat parameter comprises a volume parameter;
      based on a correlation function, the value, and the sweat parameter, determining an intoxication metric, wherein the intoxication metric comprises a predicted time until sober, and wherein the predicted time until sober decreases as a value of the sweat parameter increases; and
   at the transdermal alcohol sensing device:
      transitioning to a second operation mode, wherein in the second operation mode, the transdermal alcohol sensing device does not transmit information to the client application.

2. The method of claim 1, wherein the value associated with the set of signals comprises an averaged value of the set of signals.

3. The method of claim 2, further comprising comparing the average value with a set of average values previously received at the user device.

4. The method of claim 3, further comprising removing redundant average values from memory of the user device.

5. The method of claim 1, further comprising providing a notification to the user based on the intoxication metric, wherein the notification is provided to at least one of the transdermal alcohol sensing device and the user device.

6. The method of claim 5, wherein the client application is in communication with a second client application executing on the user device, wherein the notification comprises a message associated with the second client application.

7. The method of claim 6, further comprising at the first client application, triggering an action with the second client application.

8. The method of claim 1, wherein the notification comprises an estimated number of drinks consumed by the user.

9. The method of claim 8, wherein determining the estimated number of drinks consumed by the user comprises determining an area underneath a BAC curve, the BAC curve determined at least in part based on a set of TAC values determined from the set of samples.

10. A method for monitoring intoxication of a user, the method comprising:
    at a transdermal alcohol sensing device coupled to a wrist region of the user:
       receiving a set of samples from a skin surface of the user;
       determining a set of signals at a sensor of the transdermal alcohol sensing device based on the set of samples;
       selectively transmitting a value associated with the set of signals to a client application executing on a user device;
    at the client application:
       receiving the value;
       determining a transdermal alcohol content (TAC) value based on the value;
       determining a sweat parameter associated with the set of samples, wherein the sweat parameter comprises a volume parameter;
       based on a correlation function, the TAC value, and the sweat parameter, determining a predicted time until sober, wherein the predicted time until sober decreases as a value of the sweat parameter increases;
    providing a notification based on the predicted time until sober at one or both of the transdermal alcohol sensing device and a display associated with the user device.

11. The method of claim 10, wherein the value associated with the set of signals comprises an averaged value of the set of signals.

12. The method of claim 11, further comprising comparing the average value with a set of average values previously received at the user device.

13. The method of claim 12, further comprising removing redundant average values from memory of the user device.

14. The method of claim 10, wherein the client application is in communication with a second client application executing on the user device, wherein the notification comprises a message associated with the second client application.

15. The method of claim 14, wherein the second client application comprises a transportation application.

16. The method of claim 14, further comprising at the first client application, triggering an action with the second client application.

17. The method of claim 10, further comprising receiving a second sample from the user at a second device separate and distinct from the transdermal alcohol sensing device, wherein the second sample is received contemporaneously with the first sample, wherein the correlation function is determined based on the second sample.

18. The method of claim 17, wherein the second sample comprises a breath sample.

* * * * *